US010174282B2

United States Patent
Lee et al.

(10) Patent No.: US 10,174,282 B2
(45) Date of Patent: Jan. 8, 2019

(54) METHOD FOR MASS CULTURING PHOTOSYNTHETIC MICROALGAE BY ADDITIONALLY SUPPLYING ENVIRONMENTAL WATER

(71) Applicant: Inha-Industry Partnership Institute, Incheon (KR)

(72) Inventors: Choul Gyun Lee, Seoul (KR); Hanwool Park, Incheon (KR); Z Hun Kim, Incheon (KR); Sang Min Lim, Incheon (KR); Dong-Woo Shin, Chungcheongbuk-do (KR); Philhan Kim, Seoul (KR); Dan Bee Yoo, Bucheon-si (KR); Daewoo Jung, Tongyeong-si (KR); Jong Chan Lee, Seoul (KR)

(73) Assignee: Inha-Industry Partnership Institute, Incheon (KR)

(*) Notice: Subject to any disclaimer, the term of this patent is extended or adjusted under 35 U.S.C. 154(b) by 30 days.

(21) Appl. No.: 15/304,645

(22) PCT Filed: Dec. 18, 2014

(86) PCT No.: PCT/KR2014/012523
§ 371 (c)(1),
(2) Date: Oct. 17, 2016

(87) PCT Pub. No.: WO2015/160068
PCT Pub. Date: Oct. 22, 2015

(65) Prior Publication Data
US 2017/0044484 A1    Feb. 16, 2017

(30) Foreign Application Priority Data
Apr. 18, 2014  (KR) ........................ 10-2014-0046662

(51) Int. Cl.
*C12M 1/00* (2006.01)
*C12N 1/12* (2006.01)

(52) U.S. Cl.
CPC ............... *C12N 1/12* (2013.01); *C12M 21/02* (2013.01); *C12M 23/18* (2013.01); *C12M 29/04* (2013.01)

(58) Field of Classification Search
CPC ..................................................... C12M 23/02
See application file for complete search history.

(56) References Cited

U.S. PATENT DOCUMENTS

2009/0130706 A1    5/2009  Berzin et al.
2012/0122199 A1*   5/2012  Kabakian ............... C12M 21/02
                                                  435/292.1
2013/0052719 A1*   2/2013  Lee ......................... C12M 21/02
                                                  435/257.1

FOREIGN PATENT DOCUMENTS

JP      2007-330215 A    12/2007
KR   10-2010-0063260 A     6/2010
(Continued)

*Primary Examiner* — Rosanne Kosson
(74) *Attorney, Agent, or Firm* — Vorys, Sater, Seymour & Pease LLP; Mih Suhn Koh

(57) ABSTRACT

The present invention relates to a method for culturing microalgae, including: (a) immersing a photobioreactor including a culture container through which a culture solution but not microalgae passes into environmental water; and (b) supplying additional environmental water into the culture container. Through the present invention, it is expected that microalgae can be economically and efficiently mass cultured.

13 Claims, 34 Drawing Sheets

(56) References Cited

FOREIGN PATENT DOCUMENTS

KR  10-2012-0021566 A  3/2012
KR  10-1385939 B1  4/2014

* cited by examiner ic microalgae by additional supply of environmental water, and more particularly to a method for culturing microalgae including: (a) immersing a photobioreactor including a culture container through which a culture solution but not microalgae passes into environmental water; and (b) supplying additional environmental water to the culture container.
METHOD FOR MASS CULTURING PHOTOSYNTHETIC MICROALGAE BY ADDITIONALLY SUPPLYING ENVIRONMENTAL WATER

BACKGROUND OF THE INVENTION

Field of the Invention

The present invention relates to a method for mass culturing photosynthetic microalgae by additional supply of environmental water, and more particularly to a method for culturing microalgae including: (a) immersing a photobioreactor including a culture container through which a culture solution but not microalgae passes into environmental water; and (b) supplying additional environmental water to the culture container.

Background Art

Due to global warming and rapid increase of world population, food problem, environmental problem and energy problem globally occur. Due to recent rapid increase in crude oil price, development of alternative energy employing bioresources, in particular production of biofuel (e.g., bioethanol, biodiesel, biogas, etc.) receives attention. Particularly, biofuel produced from photosynthetic microorganism microalgae, which are widely distributed in seawater or plain water, is recognized as a third generation biofuel of the future following a first generation biofuel using so-called crop resources and a second generation of biofuel using stems of crops or waste wood.

It has been known that microalgae are photosynthetic organisms, which synthesize organic substances and produce oxygen by employing carbon dioxide and water in the air and underwater as a raw material through light energy, and absorb and convert carbon dioxide at a similar level to the ground plants on earth. Biodiesel production per unit area of microalgae is about 58,700 ha (oil concentration of 30%) which corresponds to 130 times of that of soybean (i.e., 446 l/ha). Moreover, high-density and massive culture of microalgae is available and molecular modification of microalgae using transformation technique, which is a key of bioengineering technology, seems to be easier than that of higher plant. In addition, there is advantage in that microalgae do not compete with crops, so that biofuel can be produced by using unemployed land.

However, to practice beneficial results such as removal of carbon dioxide or production of biofuel by using microalgae, which are photosynthetic monocellular microorganisms, high concentration culture, mass culture, or high concentration-mass culture of microalgae is required. Therefore, a culturing method capable of high concentration culture, mass culture, or high concentration-mass culture is essentially required.

Typically, a culturing method using various photobioreactions installed indoor or rooftop has been used. However, the typical method needs high cost for culturing microalgae because the method requires a lightening unit and supply and mixing unit of medium or gas, so that mass culture of microalgae, which is required for commercialization, is difficult. Therefore, for mass culture of microalgae at a commercialized scale, secure of economic feasibility is a prior task. Also, it is urgently required to develop a culturing method capable of high concentration culture with low-cost and easier scale-up.

Korean Registered Patent No. 1385939 discloses "a photobioreactor for mass culture of microalgae and a method for culturing microalgae using the same" and Korean Laid-open Patent Publication No. 2012-0021566 discloses "a method for culturing photosynthetic microalgae by co-culture". However, there is no statement about a method for mass culturing photosynthetic microalgae through additional supply of environmental water.

SUMMARY OF THE INVENTION

Technical Problem

The present invention is derived to the need as described above, and the present invention has been completed by confirming that, as a result of supplying nutrients to a photobioreactor through additional supply of environmental water, culture of microalgae is available by using environmental water having low nutrient content such as natural seawater as well as artificial seawater.

Technical Solution

To solve the problems described above, the present invention provides a method for culturing microalgae including: (a) immersing a photobioreactor including a culture container through which a culture solution but not microalgae passes into environmental water; and (b) supplying additional environmental water into the culture container.

Advantageous Effects

In the culturing method using a typical photobioreactor, since exchange of materials between environmental water and culture solution is achieved by dispersion, there is a problem in that productivity of microalgae is limited by concentration difference of nutrient and waste between environmental water and the culture solution. In the purpose of solving the problem and enhancing productivity of microalgae for economic feasibility, a culturing method having increased productivity of microalgae is developed by supplying additional environmental water including nutrients to the photobioreactor such that depletion of nutrients, which may occur during microalgae culture, is resolved. It is expected that, through the culturing method using a photobioreactor, microalgae can be economically and efficiently mass cultured.

BRIEF DESCRIPTION OF THE DRAWINGS

FIG. 2b is a cross sectional view of the photobioreactor of FIG. 2a.

● , △: polyester mesh sheet,
○ , ■: nylon mesh sheet,
▼, □: 50 kDa molecular weight cut-off, semipermeable membrane,
f/2: f/2 culture medium and
NSW: natural seawater.

Figure 17:
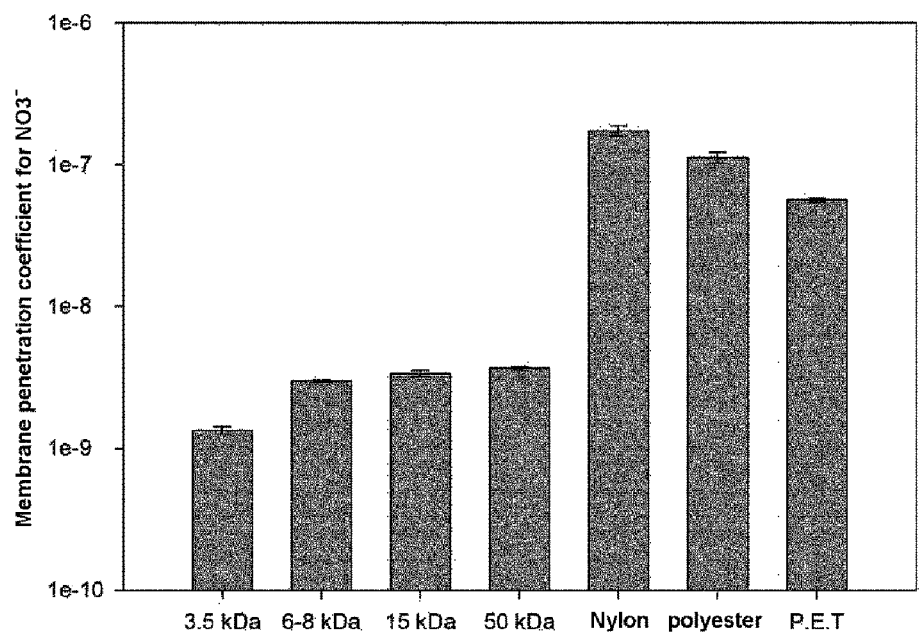

FIG. 17 is a graph showing nutritional salts permeability of a photobioreactor according to an example of the present invention.

Figure 18:
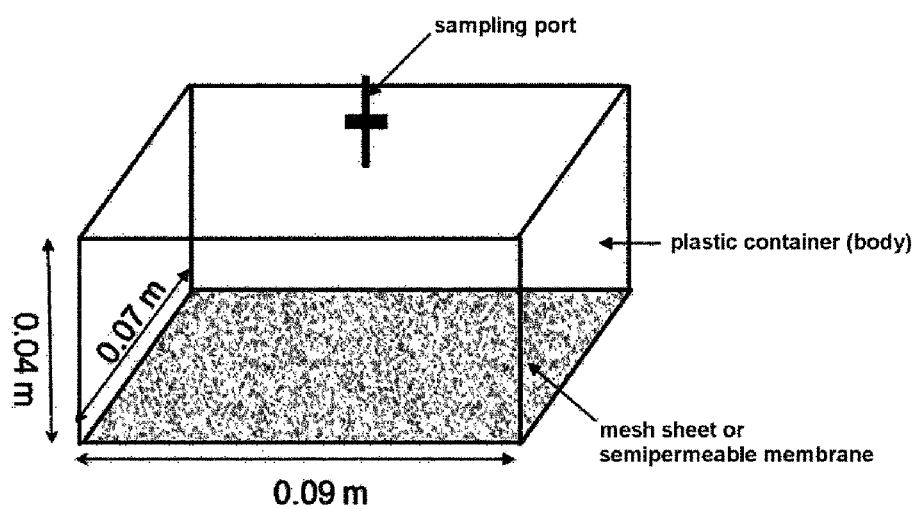

FIG. 18 is an illustration schematically showing a photobioreactor used for microalgae culture in actual sea according to an example of the present invention.

Figure 19:
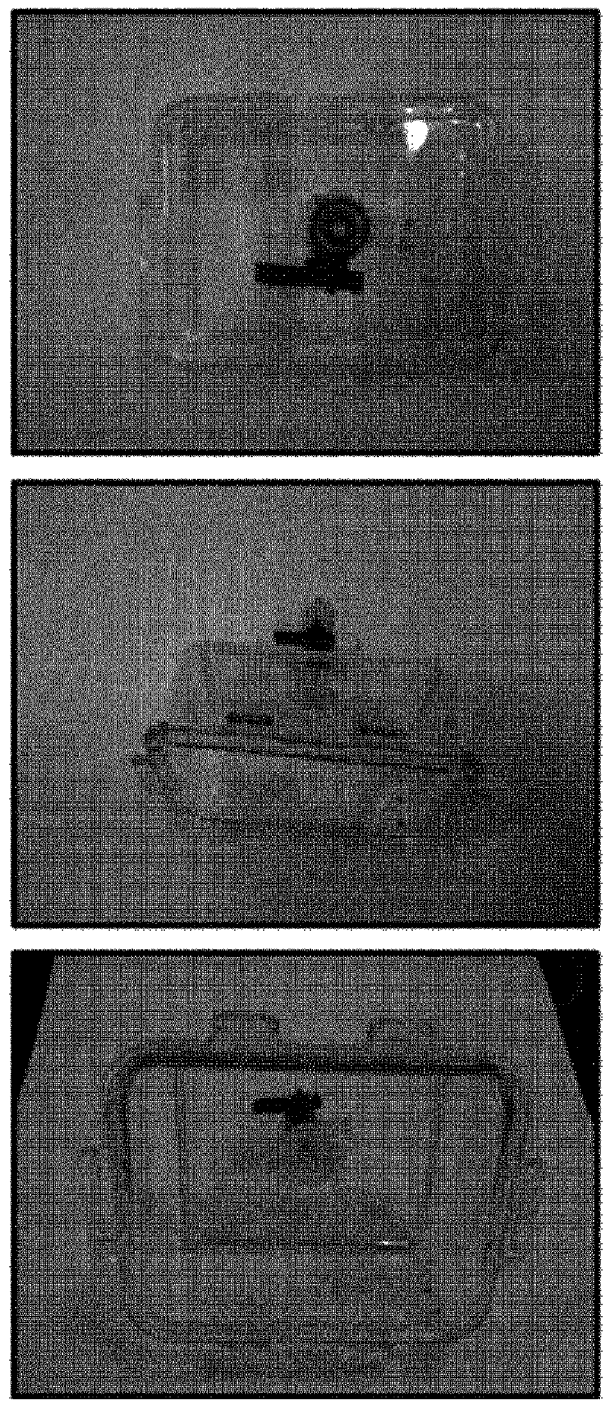

FIG. 19 is an image showing a nonpermeable plastic container used in microalgae culture in actual sea using a photobioreactor according to an example of the present invention.

Figure 20:
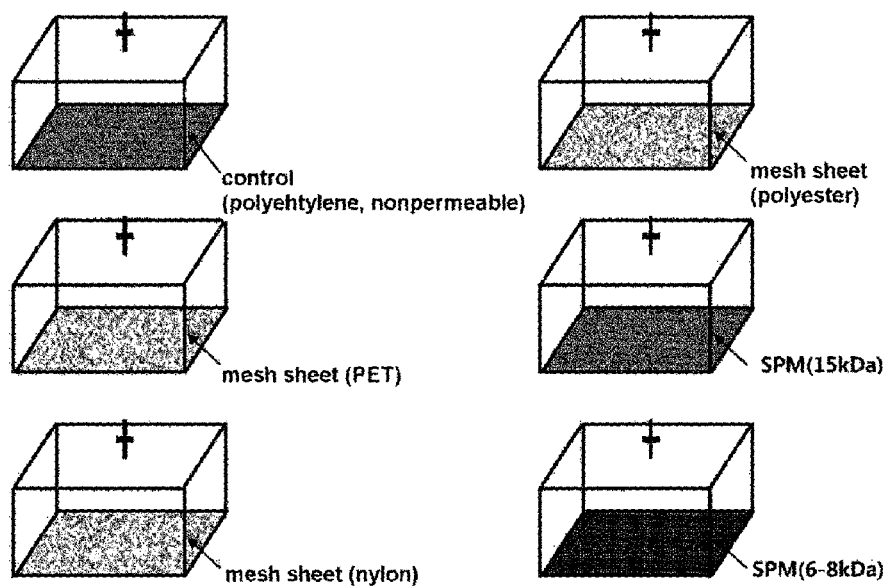

FIG. 20 is a schematic diagram showing an experimental design for culturing microalgae in actual sea by using a photobioreactor according to an example of the present invention.

Figure 21:
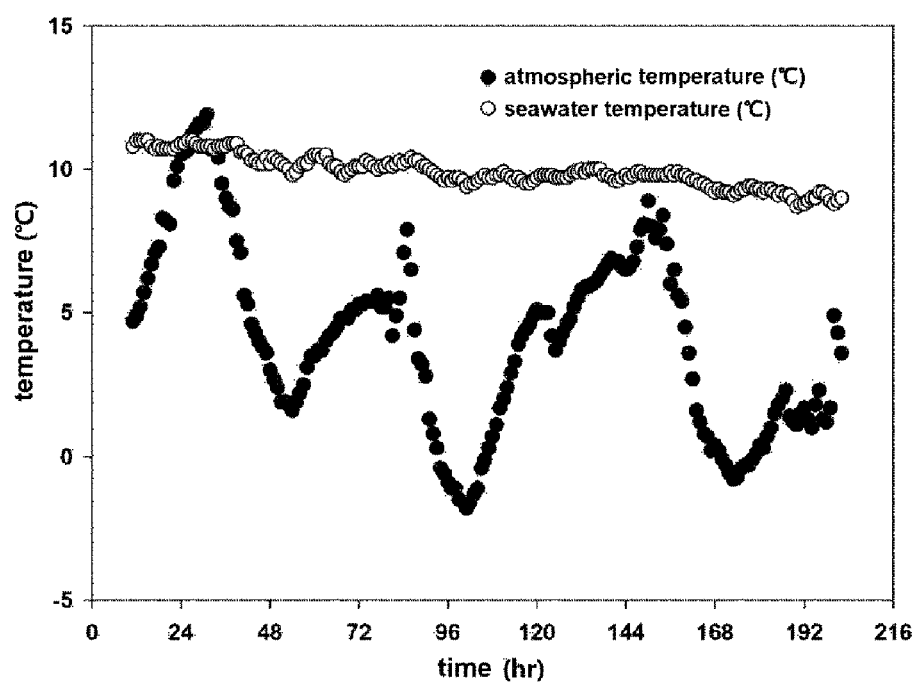

FIG. 21 is a graph showing changes in air and seawater temperature when microalgae are cultured in actual sea by using a photobioreactor according to an example of the present invention.

Figure 22A:
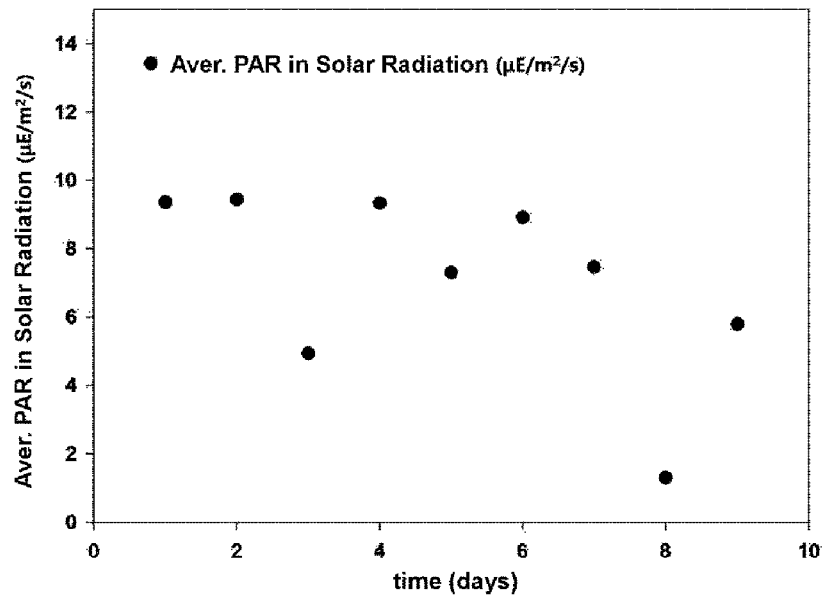
Figure 22B:
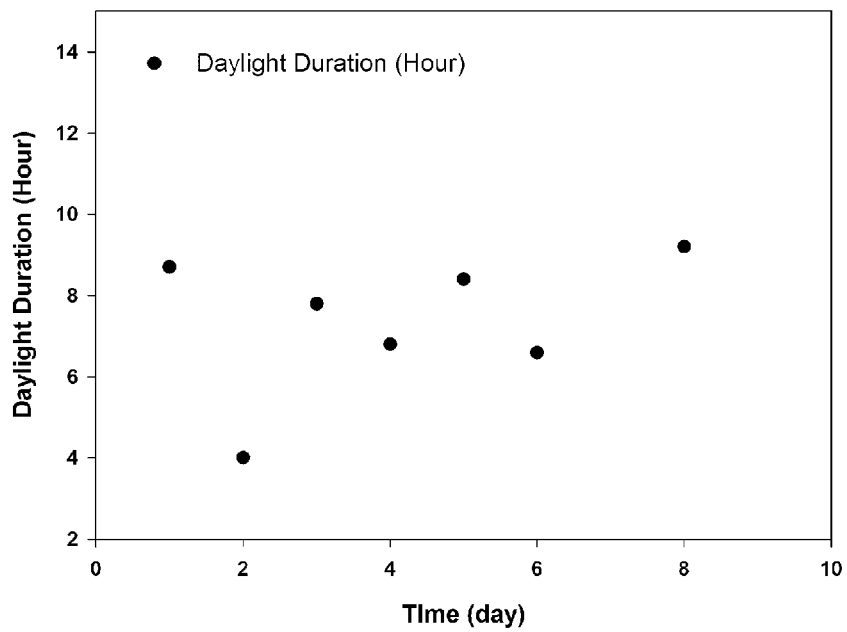

FIG. 22a is a graph showing photosynthetically active radiation (PAR) when microalgae are cultured in actual sea by using a photobioreactor according to an example of the present invention. FIG. 22b is a graph showing light irradiation time when microalgae are cultured in actual sea by using a photobioreactor according to an example of the present invention.

Figure 23A:
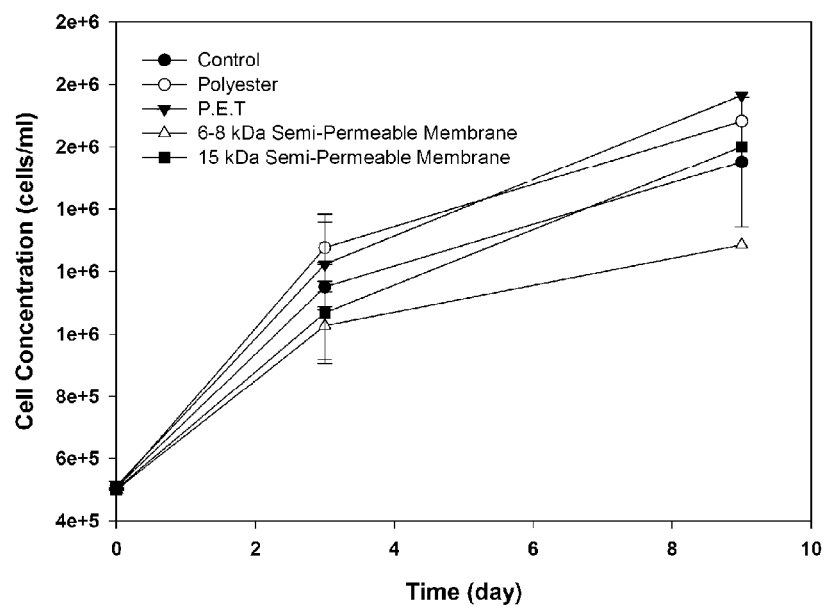
Figure 23B:
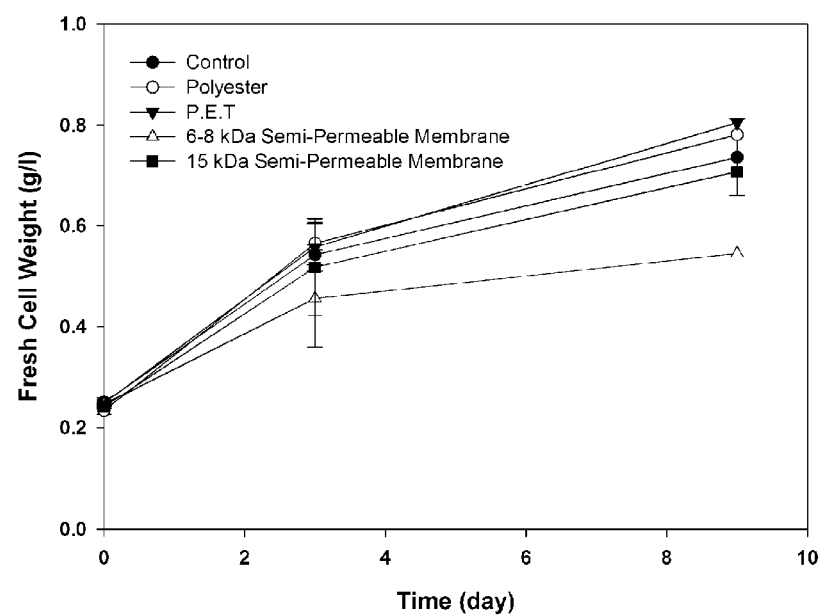

FIG. 23a is a graph showing cell concentration after the microalgae are cultured in actual sea by using a photobioreactor according to an example of the present invention. FIG. 23b is a graph showing wet weight calculated after the microalgae are cultured in actual sea by using a photobioreactor according to an example of the present invention.

Figure 24:
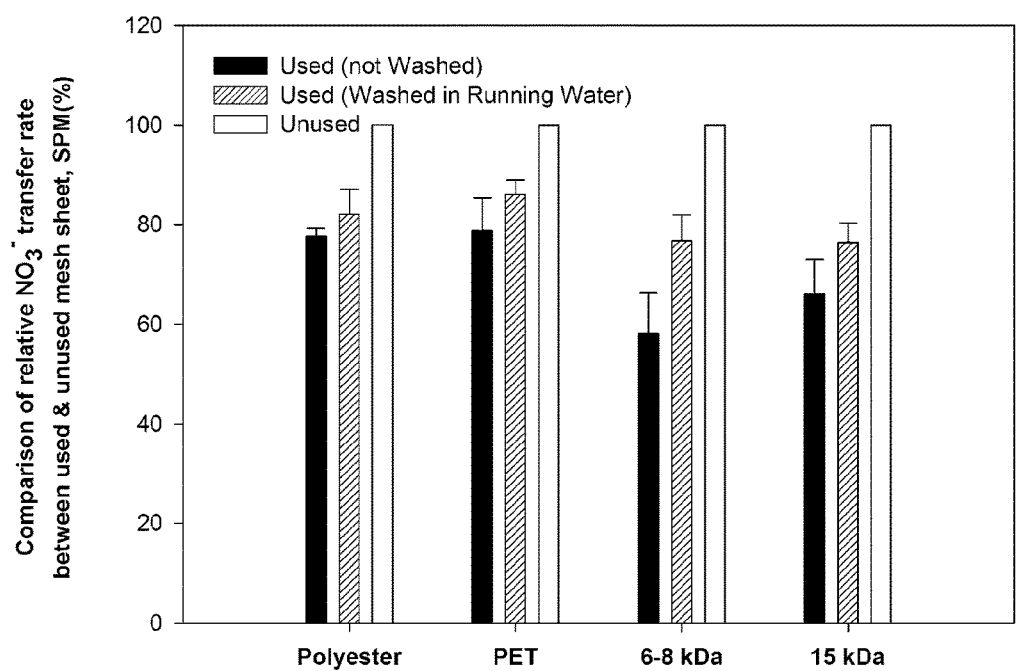

FIG. 24 is a graph comparing nitrate permeability of a photobioreactor according to an example of the present invention depending on reuse of a mesh sheet with that of a photobioreactor prepared by using a semipermeable membrane.

Figure 25:
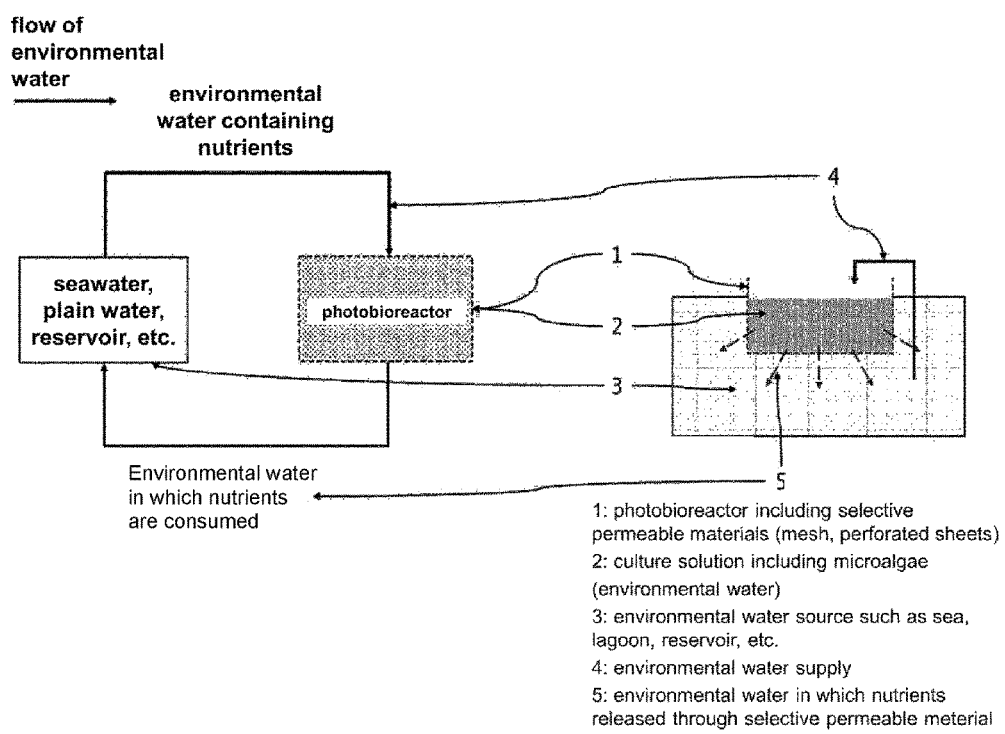

FIG. 25 is a schematic diagram of a culturing method using a photobioreactor through supply of environmental water.

Figure 26:
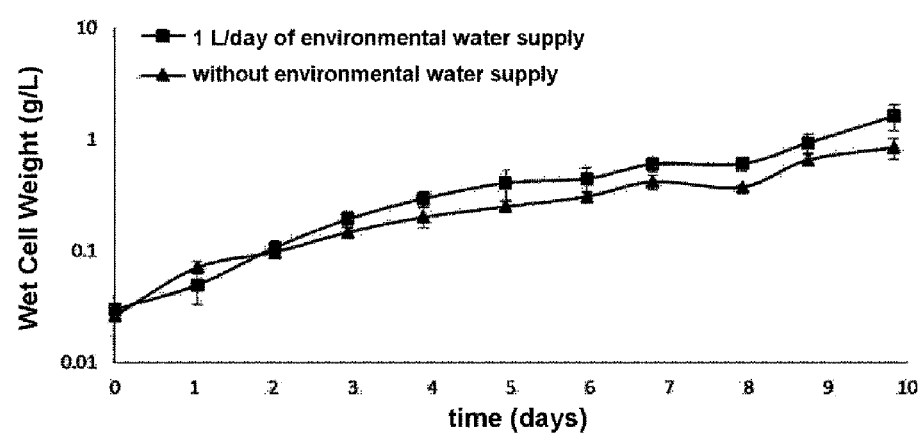

FIG. 26 is a graph showing changes in wet weight of microalgae depending on culturing time in *Dunaliella tertiolecta* culturing experiment using a photobioreactor prepared with a mesh sheet in artificial seawater.

Figure 27:
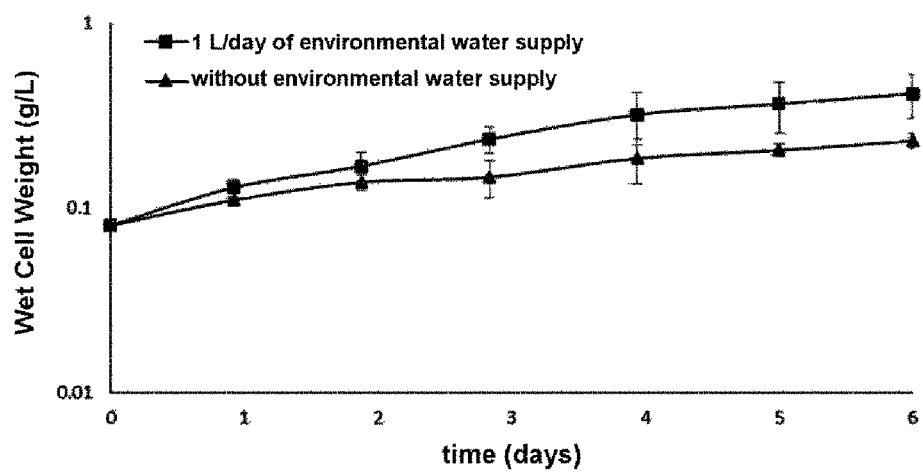

FIG. 27 is a graph showing changes in wet weight of microalgae depending on culturing time in *Tetraselmis* culturing experiment using a photobioreactor in natural seawater.

Figure 28:
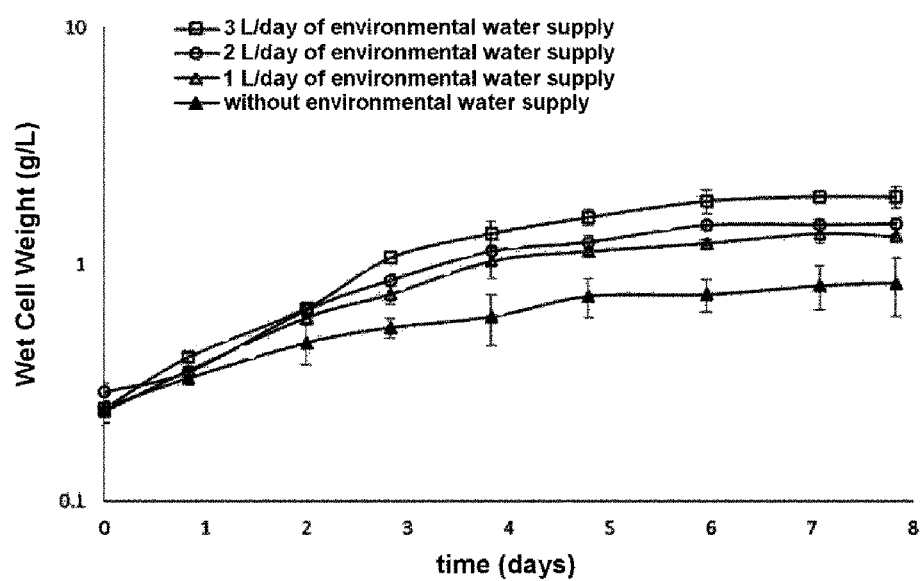

FIG. 28 is a graph showing changes in wet weight of microalgae depending on culturing time in *Tetraselmis* culturing experiment according to amounts of natural seawater supply.

Figure 29:

FIG. 29 is an image showing changes in wet weight of microalgae according to 3 l/day of environmental water supply after 7 days of culture.

Figure 30:
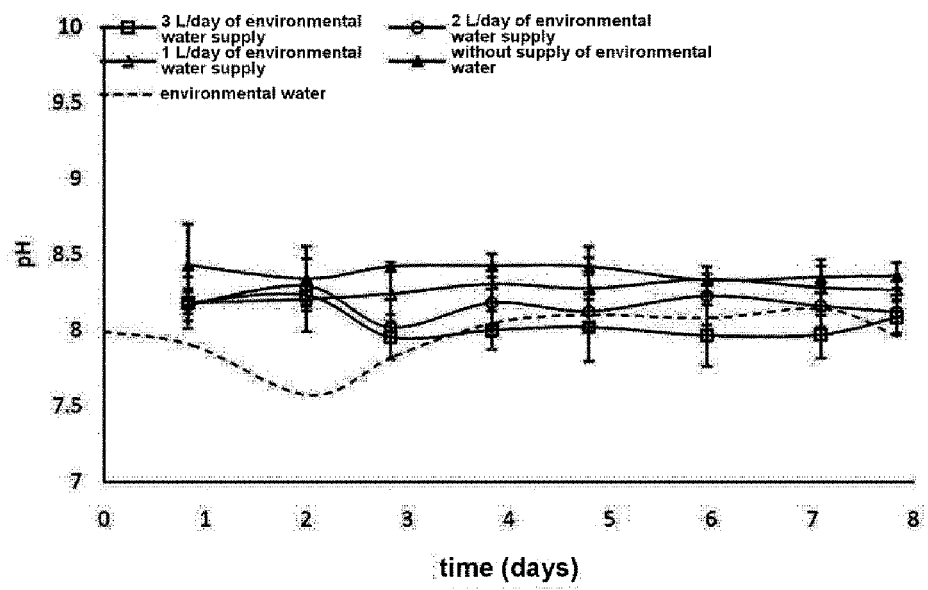

FIG. 30 is a graph showing pH changes of a culture solution according to amounts of environmental water supply.

Figure 31:
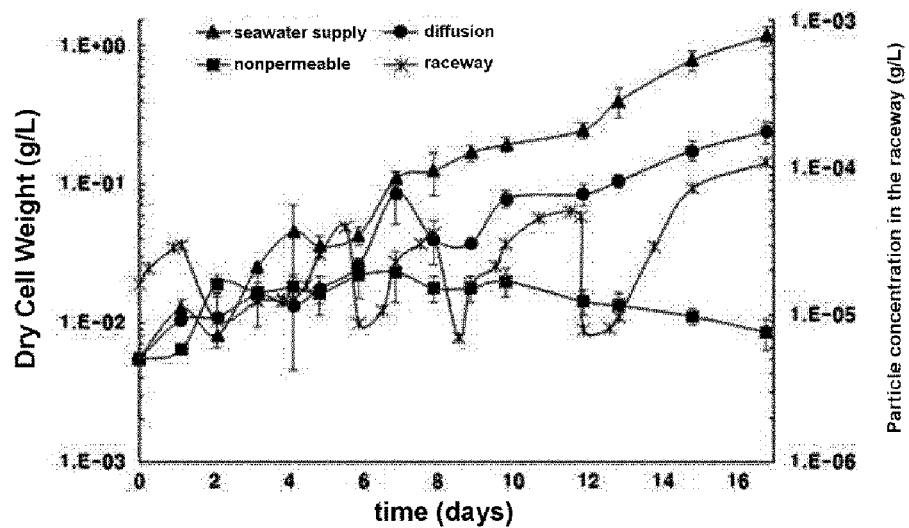

FIG. 31 is a graph showing productivity of microalgae per unit area per day depending whether natural seawater is supplied or not.

Figure 32:
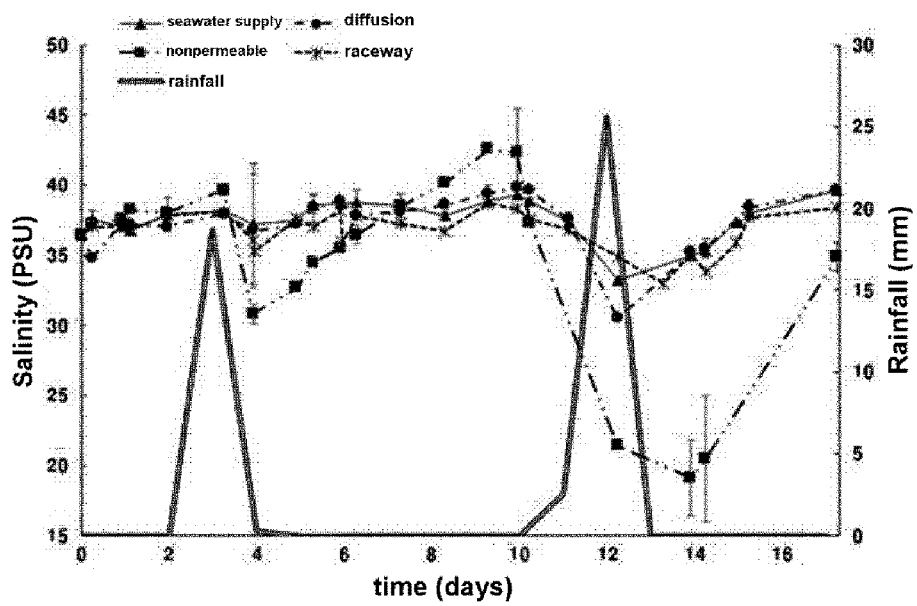

FIG. 32 is a graph showing salinity in a culture solution under the rainfall condition with continuous supply of natural seawater.

Figure 33:
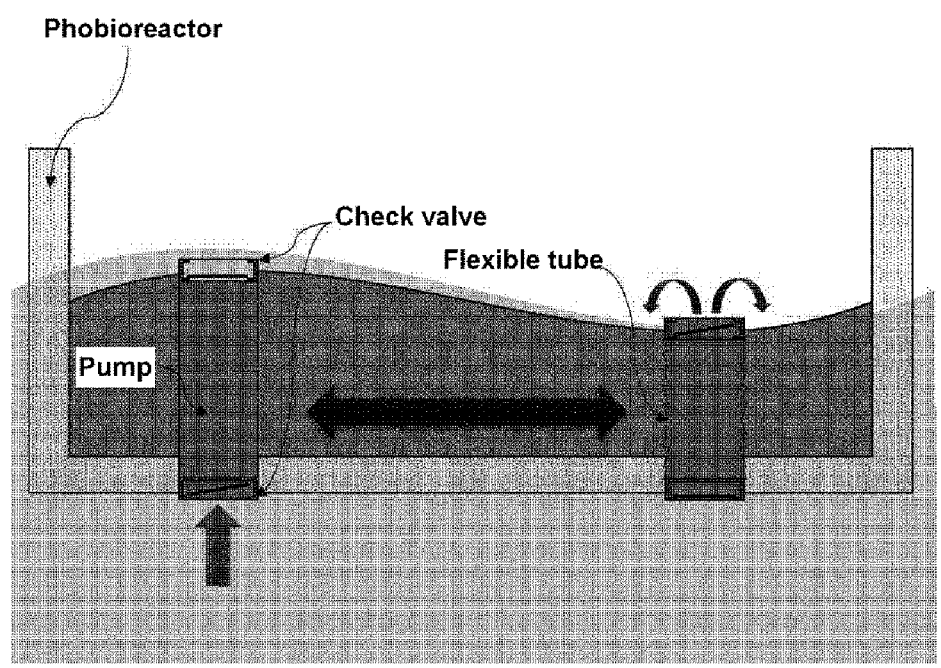

FIG. 33 is a schematic diagram of a wave pump.

Figure 34:
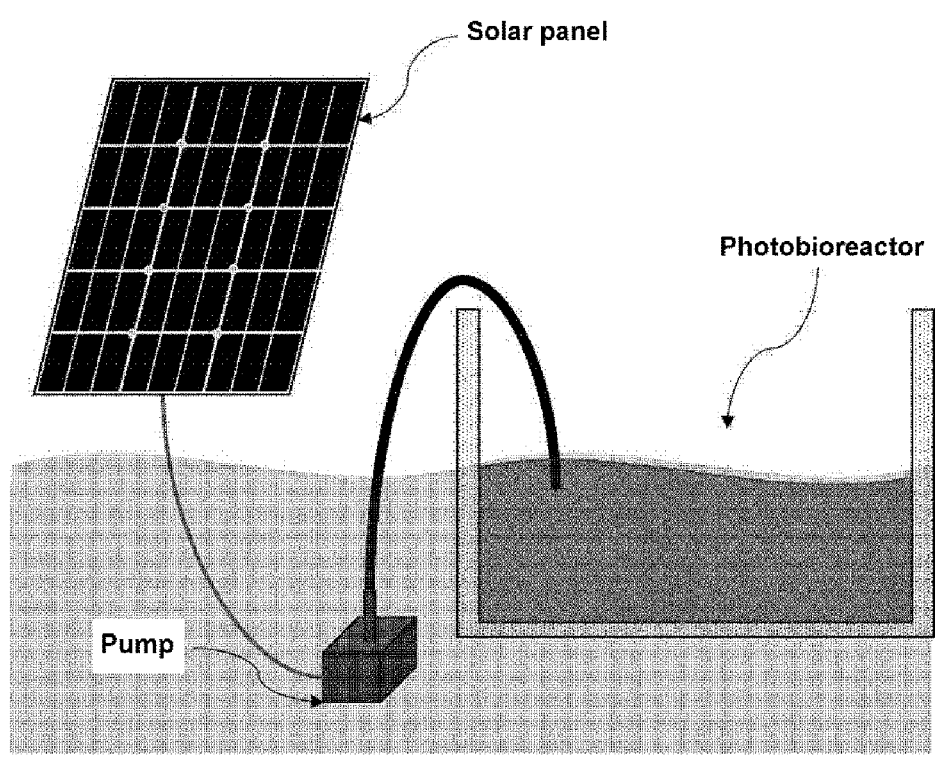

FIG. 34 is a schematic diagram of a photovoltaic pump.

DETAILED DESCRIPTION OF THE INVENTION

Mode for Carrying Out the Invention

To achieve the purpose of the present invention, the present invention provides a method for culturing microalgae, including:

(a) immersing a photobioreactor including a culture container through which a culture solution but not microalgae passes into environmental water; and (b) supplying additional environmental water into the culture container.

In an embodiment of the present invention, in step (b), the environmental water is supplied in an amount calculated from the following equation:

$$V_{min} = \frac{K_p \cdot A}{C_{salt}}$$

wherein, $V_{min}$ indicates minimal environmental water supply (l/day); $K_p$ indicates maximum penetration of nutrients (carbon, nitrogen or phosphorus) at boundary surface in the environmental water (mg/m²/day); A indicates a surface area of a mesh sheet immersed in environmental water (m²); and $C_{salt}$ indicates nutrient concentration of environmental water at the outside of a culture container (mg/l).

Also, in an embodiment of the present invention, the supplying additional environmental water in step (b) is preferably performed by using a wave pump, a sling pump, a wheel pump, or a photovoltaic pump without supply of external power, but not limited thereto.

As shown in FIG. 33, the wave pump which pumps water using a force obtained through vertical movement of seawater such as land swell or wave through a check valve and flexible tube. The sling pump and wheel pump use, as a power, rotatory power caused by flow of water. A water hammer pump which pumps water by using energy of water passing through a circular tube from a higher place through water hammering. A wind pump uses, as a power, electricity produced through a turbine which is rotated by wind or rotatory power itself. As shown in FIG. 34, the photovoltaic pump obtains electrical power by using a solar panel.

In addition, in an embodiment of the present invention, the environmental water may preferably be supplied in an amount of 0.38 to 50000 l/day, and more preferably 670 to 2000 l/day based on 1 m² of the total mesh sheet size, but not limited thereto.

Additionally, in an embodiment of the present invention, the environmental water refers to water in a place where the photobioreactor of the present invention is introduced and the culture is conducted, and may include seawater, plain water, brackish water, domestic sewage, artificially prepared medium, or eutrophic contaminated water, as well as water from artificially prepared water reservoir or pond.

In an embodiment of the present invention, the seawater refers to natural seawater or artificial seawater prepared to have ion composition, osmotic pressure and pH approximate to those of seawater.

Nutrients are materials to be taken by organisms for nutrition, and include organic nutrients such as carbohydrates, lipids, proteins and vitamins and inorganic salts such as ammonium, nitrate, iron, sodium salt, potassium salt, phosphate, and magnesium salt excluding oxygen for respiration, carbon dioxide and water for photosynthesis.

Also, in an embodiment of the present invention, the microalgae may be dispersed and cultured in a culture medium without a carrier.

In addition, in an embodiment of the present invention, a whole or part of the boundary surface of the culture container may have a mesh sheet having a mesh size of 0.1 to 200 μm or a perforated sheet having a micropore size of 0.1 to 200 μm, but not limited thereto.

The mesh size of the mesh sheet and the perforating size of the perforated sheet may be adjusted according to the size of microalgae to be cultured. For examples, the mesh size of perforating size may be 2 to 5 mm, 1 to 5 mm, 0.1 μm to 200 μm, 0.1 μm to 100 μm, 0.2 μm to 50 μm, 0.5 μm to 25 μm, 0.5 μm to 10 μm, 0.7 μm to 7 μm, 1 μm to 5 μm, or 1 μm to 3 μm. Optionally, the pore size may be 50% to 300%, 70 to 250%, 85% to 200%, 90% to 160%, 100% to 150%, 100% to 140%, 100% to 130% or 110% to 120% of the size of a photosynthetic microorganism to be cultured.

The size of microalgae may be increased by being bound to each other or aggregated, so that the mesh size of the mesh sheet or perforating size of the perforated sheet may be larger than the size of microalgae mono cell.

The mesh sheet may be may be woven with a pattern, for example plain weave, twill weave, and warp stain to include a structure woven by crossing weft threads and warp threads in a vertical direction (FIG. 1), or be prepared by varying processing methods or types of a sheet material used such as compound weaving, pile weaving, and leno weaving. The mesh sheet refers to a sheet prepared by applying a technique used in preparation of a woven fabric. The mesh sheet having a woven structure allows gas, water and nutrients to freely pass through, but restricts pass of microalgae so that the mesh sheet may be economically and conveniently applied to mass production of microalgae.

The term "mesh size" refers to a size of a space between weft threads and warp threads which are woven to cross each other in the mesh structure.

The term "perforated sheet" refers to a sheet having holes by artificially perforating a planar material, wherein the planar material may be a film and the film may be a non-permeable or semipermeable membrane. Through artificial perforation, the perforated sheet may provide the same effect as the mesh sheet.

The perforated sheet may be prepared by irregularly or regularly perforating a polymer membrane by using a micro perforating device. The perforated sheet differs from a typical semipermeable membrane in that the perforated sheet is prepared by artificially perforating a non-permeable or semipermeable polymer membrane.

The term "free pass" refers to a state in which a certain material is available to pass through spaces separated by a mesh sheet or perforated sheet without limitation, wherein pass is a concept irrelevant to a concentration difference of a certain material in both spaces, while diffusion refers to a phenomenon in which a certain material migrates from a space having a higher concentration into a space having a lower concentration.

Specifically, the mesh sheet or perforated sheet allows environmental water, gas and nutrients to freely pass through, while of microalgae or contaminant microorganism are blocked. More specifically, enabling introduction of environmental water, nutrients required for growth of microalgae may be supplied and waste generated during growth of microalgae may be removed together with the environmental water. Since an additional nutrient supplier and purifier are not required, there is an effect of saving costs, time and labor. In addition, supply of carbon dioxide required for the photosynthesis process of microalgae and release of generated oxygen may be achieved through the mesh sheet. Moreover, since microalgae is cultured in a manageable restricting culture container, environmental contamination due to mass culture of microalgae may be prevented, and mass cultured microalgae may be easily harvested.

Further, in an embodiment of the present invention, except the boundary surface of the culture container having the mesh sheet or perforated sheet, the remainder boundary surface has a nonpermeable or semipermeable and transparent or translucent material.

The term "semipermeable" refers to a phenomenon in which some materials selectively pass through an interface such as a membrane or plate, and counteracts permeable indicating that most of materials are available to pass through, and nonpermeable indicating that most of materials are unavailable to pass.

The term "translucent" refers to a phenomenon in which some of light passes through an interface such as a membrane or plate, and counteracts transparent indicating that most of light pass through, and opaque indicating that pass of light is substantially blocked.

The mesh sheet and perforated sheet differ from the semipermeable membrane in that the semipermeable membrane restricts penetration of macrocmolecules having a certain size or greater such as proteins, while the mesh sheet and perforated sheet allow macromolecules except materials having a cell size to freely pass through.

The mesh sheet may be woven with a polymer fabric. The polymer may be a biodegradable polymer or hardly degradable polymer. The biodegradable polymer may be one or more selected from the group consisting of polycaprolactone, poly lactic acid, poly(lactic-co-glycolic acid), cellulose, methyl cellulose, ethyl cellulose, cellulose acetate, curdlan, polyglutamic acid, polylysine, polyhydroxy alkanoate, polyethylene glycol, polyglycolic acid, and polyester, but not limited thereto.

In addition, the hardly degradable polymer may be one or more selected from the group consisting of teflon (polytetrafluoroethylene), polyolefine, polyamides, polyacrylate, silicon, poly methyl methacrylate, polystyrene, ethylene-vinyl acetate copolymer, polyethylene-maleic anhydride copolymer, polyamide, polyvinyl chloride (PVC), polyvinyl fluoride, poly vinyl imidazole, chlorosulphonate polyolefin, polyethylene terephthalate (PET), nylon, low density polyethylene (LDPE), high density polyethylene (HDPE), acryl, polyetherketone, polyimide, polycarbonate, polyurethane, and polyethylene oxide, but not limited thereto.

The nonpermeable polymer may be one or more selected from the group consisting of teflon (polytetrafluoroethylene), polyolefine, polyamides, polyacrylate, silicon, poly methyl methacrylate, polystyrene, ethylene-vinyl acetate copolymer, polyethylene-maleic anhydride copolymer, polyamide, polyvinyl chloride, polyvinyl fluoride, poly vinyl imidazole, chlorosulphonate polyolefin, polyethylene terephthalate (PET), nylon, low density polyethylene (LDPE), high density polyethylene (HDPE), acryl, polyetherketone, polyimide, polycarbonate, polyurethane, and polyethylene oxide, but not limited thereto.

The semipermeable polymer membrane may be one or more hydrophilic polymer selected from the group consisting of cellulose, methyl cellulose, ethyl cellulose, cellulose acetate, polyvinyl alcohol, cellophane, nitrocellulose and polyester, and may be prepared with a complex material of the hydrophilic polymer and the polymer fabric of the nonpermeable polymer membrane.

Figure 2A:
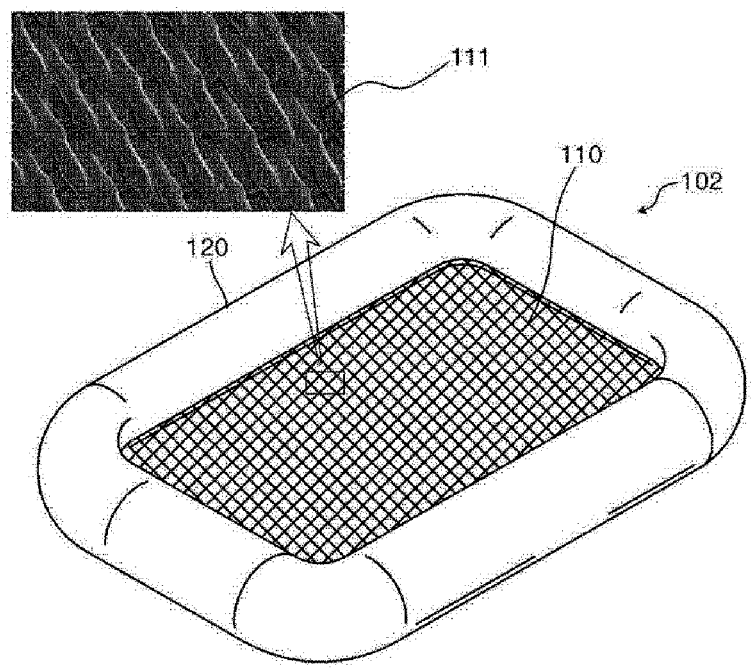
FIG. 2a is an illustrative drawing of a photobioreactor having a culture container to which a tube-type floating unit is coupled.
Figure 4:
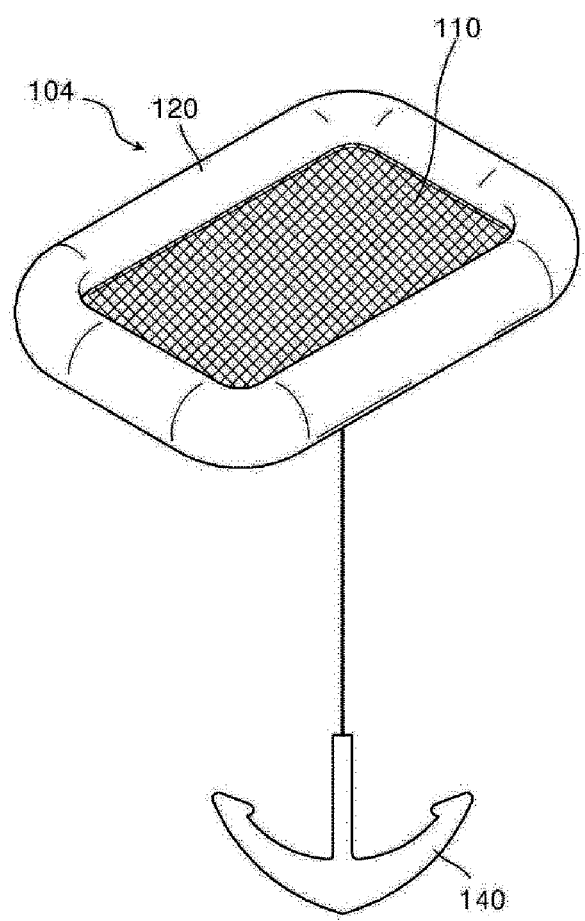
FIG. 4 is an illustrative drawing of a sedimentation unit coupled to the lower part of a culture container to allow the culture container to be submerged under the water surface at a certain depth.
Figure 5:
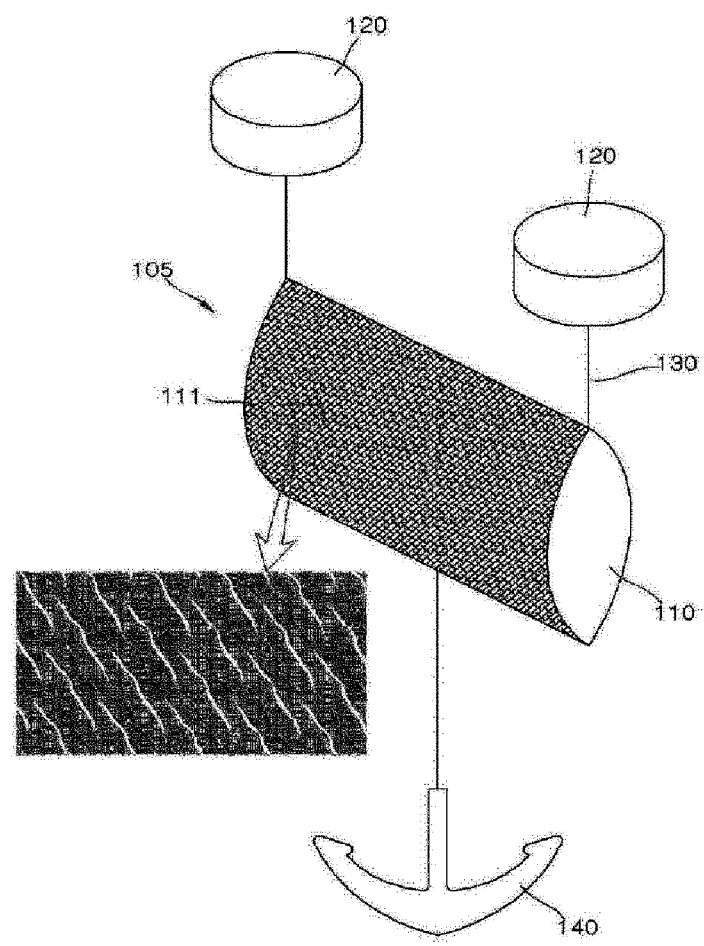
FIG. 5 is an illustrative drawing of a culture container having one end coupled to a couple of floating units and the other end coupled to a sedimentation unit.

Additionally, in the photobioreactor according to an embodiment of the present invention, the culture container may be floated on the water surface through the floating unit (FIGS. 2a and b, and 5) or may be submerged under the water through the sedimentation unit (FIGS. 4 and 5). The floating unit may be a floater such as a buoy separately placed outside of the culture container (FIG. 5) or may be in a shape of an air injectable tube which is not separately installed but extended from the culture container (FIGS. 2a and b). In addition, the sedimentation unit may be a plumb bob coupled to the lower part of the culture container (FIGS. 4 and 5), or an underwater structure placed underwater or under the water surface to allow the culture container to be submerged under the water surface at a certain depth.

Further, one end of the culture container may be coupled to the floating unit and the other end may be coupled to the sedimentation unit (FIG. 5).

Figure 6A:
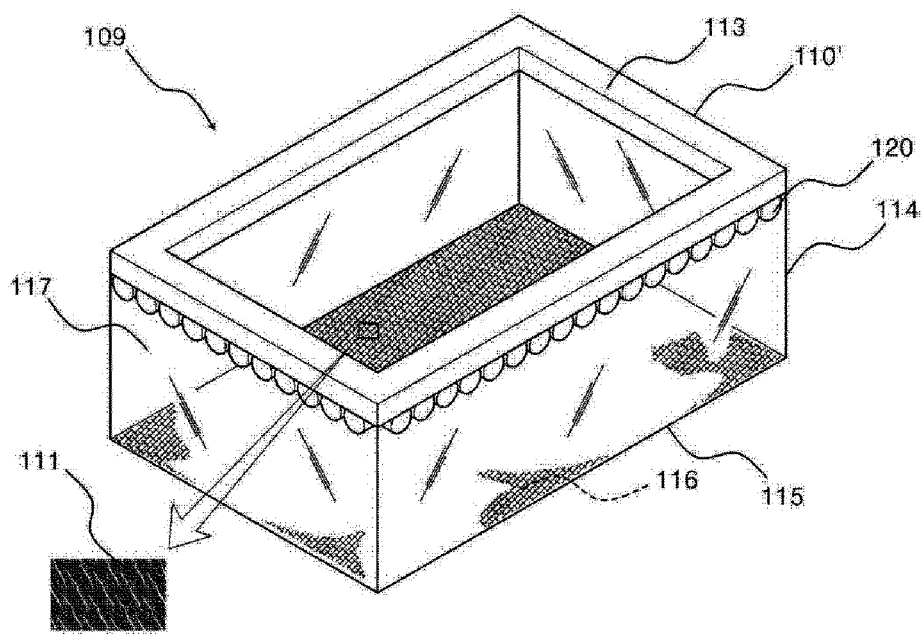
FIG. 6a is an illustrative drawing of a cage-type photobioreactor which is placed to float on the water surface.
Figure 6B:
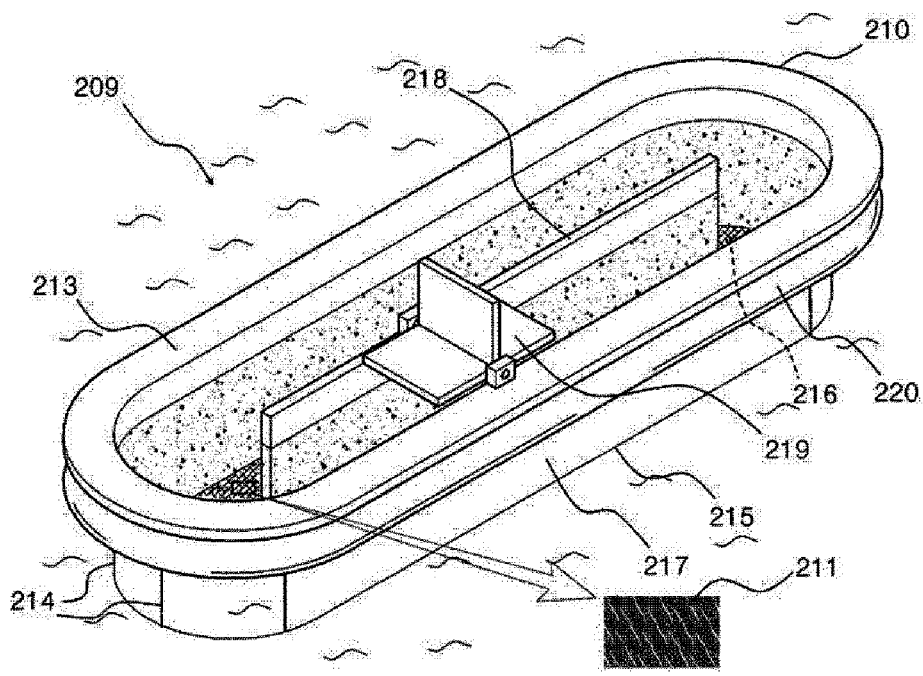
FIG. 6b is an illustrative drawing of a raceway pond-type photobioreactor which is placed to float on the water surface.

In addition, the culture container may be an enclosed-type culture container or an open-type culture container having an opened upper face (FIGS. 6a and b), wherein the open-type culture container may have a raceway-shaped pond structure (FIG. 6b), and may further include a culture solution circulator to circulate the culture solution (FIG. 6b).

The open-type culture container may include an upper frame, and a boundary surface which is coupled to the upper frame to hold microalgae. A whole or part of the boundary surface is prepared with a material which allows water, gas, and nutrients to freely pass through, but restricts free pass of the microalgae. Further, the open-type culture container may additionally include a vertical frame and a lower frame (FIGS. 6a and b). The upper frame may be prepared with a buoyant material (FIG. 6b) or additionally include a floating unit (FIG. 6a). When the upper frame is prepared with the buoyant material, the frame may be a plastic frame or tube having a vacuum inside or including air or gas capable of providing buoyancy (FIG. 6b). As necessary, the upper frame may hold the boundary surface to thereby regulate the depth of the culture container.

The boundary surface refers to a structure which spatially separates outside of the culture container from inside of the culture container including microalgae to be cultured. The wording "allows water, gas, and nutrients to freely pass through, but restricts free pass of microalgae" means that most of materials including macromolecules such as water, gas and nutrients are available to freely pass through, rather than a certain molecule selectively passes, however free pass of cells such as microalgae is restricted. Although some cells may pass through the boundary surface, cell concentrations both side of the boundary surface do not reach equivalent states. A semipermeable membrane differs from "the boundary surface allowing water, gas, and nutrients to freely pass through, while restricting free pass of microalgae" in that the semipermeable membrane restricts pass of gas, and considerable number of macromolecules is not available to pass through at all. The boundary surface may be, for example a mesh sheet or perforated sheet.

Figure 7:
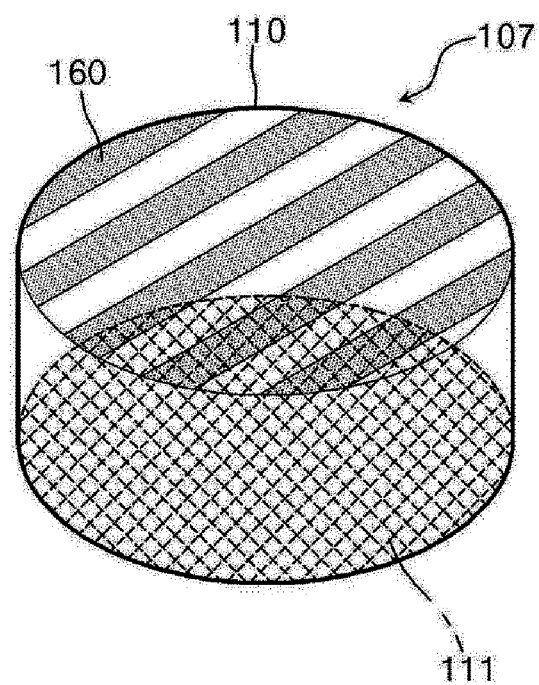
FIG. 7 is an illustrative drawing of a light blocking cover which is configured to control light energy supplied to microalgae.

Further, the photobioreactor according to an embodiment of the present invention may be configured to modulate light energy supplied to microalgae through a light blocking cover on the upper part of the culture container (FIG. 7). The light blocking cover has a light filtering function, so that only a certain region of wavelengths, among solar light supplied to the photobioreactor, may selectively penetrate or be blocked. The wavelength region may be, for example, where divided as blue, red or green series, among solar light wavelength. The wavelength region to penetrate or to be blocked may be appropriately selected depending on types of microalgae to be cultured. A membrane having the light filtering function may be prepared by mixing a plastic or polymer material with a chemical component capable of absorbing a light wavelength at a certain wavelength region. The chemical component may be included in a pigment dye.

Figure 8A:
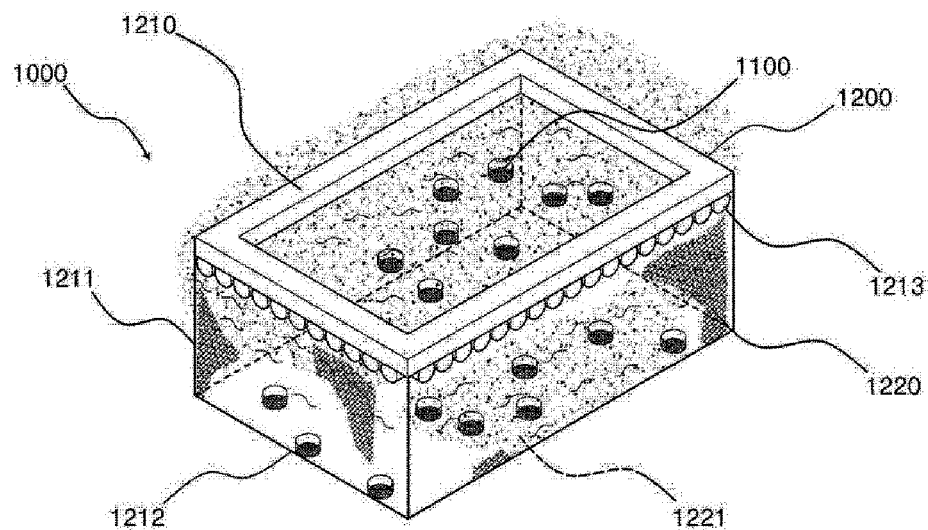
FIG. 8a is an illustrative drawing of a microalgae culturing field having a plurality of photobioreactors without a floating unit.

In addition, a plurality of photobioreactors coupled to each other according to an embodiment of the present invention may form a microalgae culturing field (FIGS. 8a and b).

When culturing is performed by using the microalgae culturing field, loss of the photobioreactor may be prevented without an additional securer, and the photobioreactor may be easily dropped and recovered.

Figure 15:
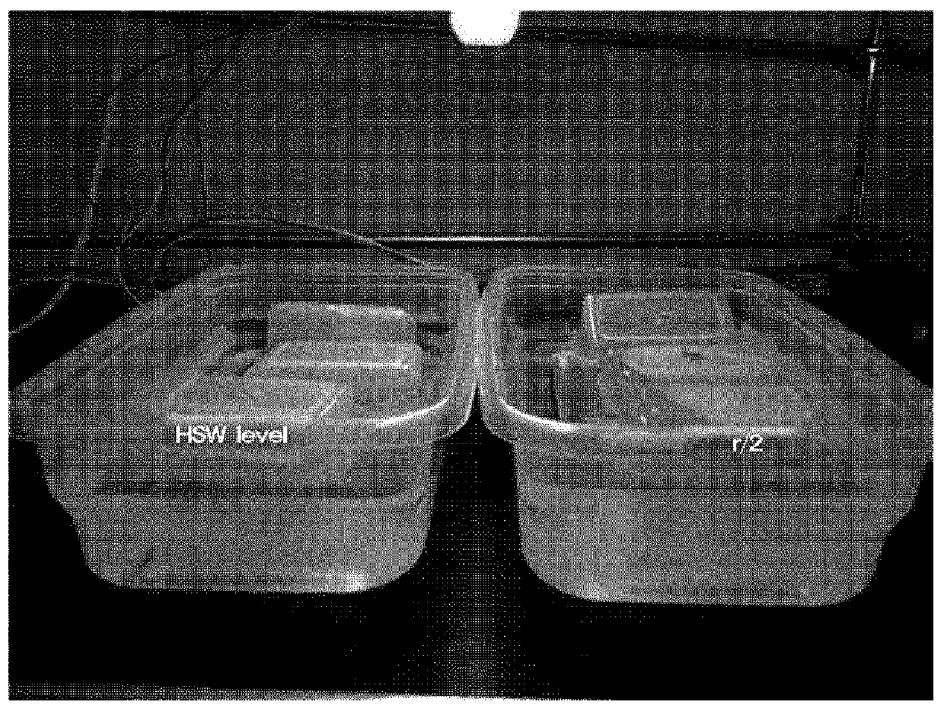
FIG. 15 is an image showing an experimental process for comparing growth rates of microalgae depending on types of the mesh sheet and semipermeable membrane used in preparation of a photobioreactor according to an example of the present invention.

A partition, which is coupled a frame to frame in order to prevent loss of the photobioreactor, is included, wherein the partition separates an inside and outside of the culturing field. The partition may be prepared with various materials such as plastics, wood, plywood, and nets, but preferably be prepared with nets in terms of costs and free communication of environmental water. The microalgae culturing field thus formed has a structure similar to a sort of floating fish cages. A floating unit may be attached to the frame of the floating structure formed on the water surface to float the floating structure onto the water surface. The floating unit may adjust buoyancy taken into account conditions such as solar light energy and nutritional salts required for microalgae to be cultured. The floating unit may be prepared with various materials such as styrofoam or a plastic vessel which has a vacuum inside or includes air or gas capable of providing buoyancy (FIGS. 15 and 19). Also, the floating unit may overlay the upper frame, or the upper frame may be coupled to a separate floating unit (FIGS. 8a and b). When the floating unit overlays the upper frame, the floating unit may serve a working space used by an operator to conduct a work in the culturing field. In addition, the floating structure may be configured to include an operator supporting unit where an operator may conduct a management work. The operator supporting unit plays a role as a support on which an operator may conduct a work, and the operator supporting unit may be coupled to the floating unit or to the underwater or floating facility separated from the floating unit. In that case, the photobioreactor may be provided with (FIG. 8b) or without (FIG. 8a) the floating unit. For the photobioreactor without the floating unit, in order not to allow the photobioreactor to be submerged under the water surface too deep, the depth of the bottom face of the floating structure may be appropriately adjusted to respond to changes in light intensity or cell concentration.

In an embodiment of the present invention, the microalgae may be green algae, red algae, or blue-green algae capable of performing photosynthesis, and preferably one or more selected from the group consisting of Chlorella, Chlamydomonas, Haematococous, Botryococcus, Scenedesmus, Spirulina, Tetraselmis, Dunaliella, Nannochloropsis, Synechococcus, Synechocystis, Nostoc, Phaeodactylum, Porphyridium, Neochloris, Chaetoceros, Isochysis, Thalassiosira, stichococcus, pyramimonas, oscillatoria, Oocystis, ochromonas, navicula, chlorococcum and Nitzschia, but not limited thereto. The microalgae described above may produce metabolite such as carotenoids, mycobiont, phycobiliproteins, lipids, carbohydrates, unsaturated fatty acids, or proteins in the culture container.

In the photobioreactor, the culture container may be provided with one or more inlets, wherein the inlet may be provided with a switching unit (FIGS. 9a and b) which may be in a form of, for example, a zipper bag, a valve, a check valve, a tub cap, an adhesive tape, a clip, or a clawclip.

In the photobioreactor, the culture container may be configured to be rotated in an axial direction by a force from water or wind through a fan attached to one face of the culture container (FIGS. 10a to d). The fan may be configured to include two or more fans extending to different directions from each other, and the fans may cross each other. In addition, the fan may have a curve to allow the culture container to be rotated on a vertical axis.

Hereinafter, embodiments of the photobioreactors illustrated in the drawings of the present invention are described. The present invention may, however, be embodied in various forms differs from each other, and should not be construed as limited to the embodiments of photobioreactors illustrated in the disclosed drawings. Rather, the embodiments of the photobioreactors illustrated in drawings are provided so that the disclosure of the present invention will be complete, and will fully convey the scope of the present invention to those skilled in the art. Also, the dimensions of elements may be exaggerated or reduced for convenience of illustration.

The photobioreactor using a mesh sheet for mass culture of microalgae according to the present invention maximizes growth rate of microalgae with minimal cost, so that microalgae may be efficiently mass-produced. Also, the photobioreactor is placed on the water surface in a floating type or is submerged under the water surface at a certain depth, so that spatial limitation in mass production overcomes.

Figure 1:
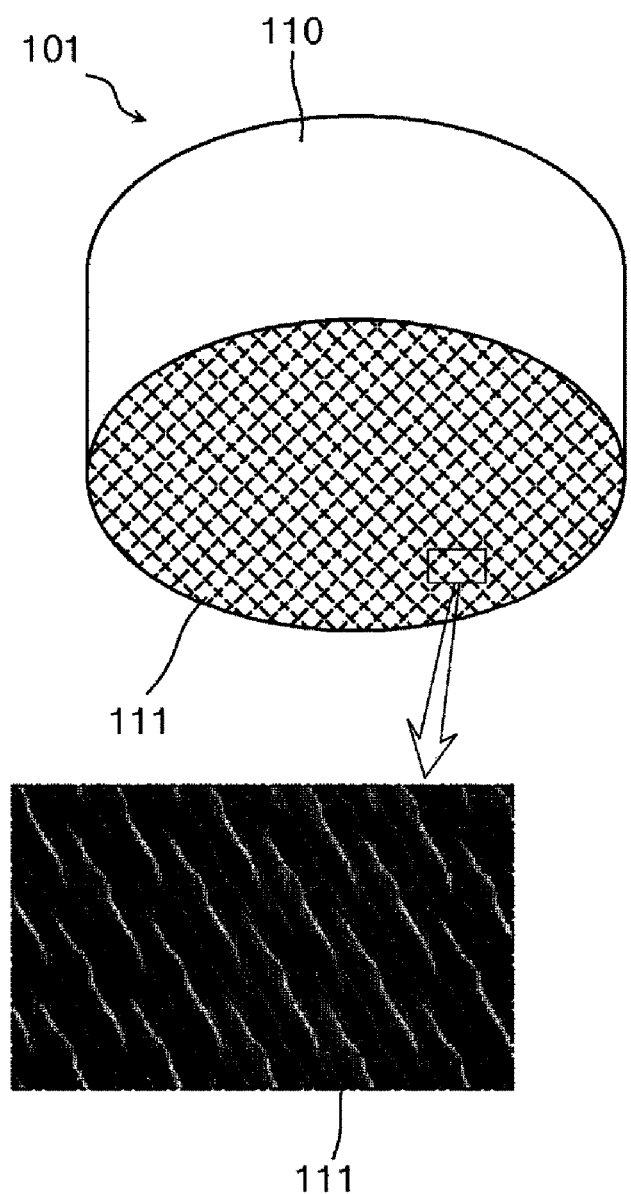
FIG. 1 is an illustrative drawing of a photobioreactor prepared with a mesh sheet.

A photobioreactor 101 as shown in FIG. 1 of the present invention includes a culture container 110 having a boundary surface a whole or part of which is prepared with a mesh sheet 111 to spatially separate environmental water from microalgae to be cultured. As the mesh sheet, likewise a perforated sheet, any material, which allows gas, water, and nutrients to freely pass through, while restricting free pass of microalgae, is available.

Specifically, the mesh sheet is characterized by allowing environmental water, gas and nutrients to freely pass through, while blocking free pass of microalgae or contaminant microorganisms. More particularly, by enabling introduction of environmental water, nutrients required for growth of microalgae may be supplied, and waste excreted during the growing process of microalgae may be removed together with environmental water. Since an additional nutrient supplier and purifier are not required, there is an effect of saving costs, time and labor. In addition, supply of carbon dioxide required for the photosynthetic process of microalgae and release of generated oxygen may be achieved through the mesh sheet. Moreover, since microalgae is cultured in a manageable restricting culture container, environmental contamination due to mass culture of microalgae may be prevented, and mass cultured microalgae may be easily harvested. In particular, the photobioreactor prepared by using the mesh sheet 111 illustrated in FIG. 1 of the present invention provides an effect of increasing growth of microalgae by about 1.5 to 2 times of that of a typical photobioreactor prepared by using a semipermeable membrane, indicating that production efficiency of the microalgae is significantly improved.

The mesh sheet allows water, nutrients, gas and waste of microalgae to be freely introduced and released, while blocking free pass of the microalgae. For example, the mesh sheet may be woven with a polymer fabric. The polymer may be a biodegradable polymer or hardly degradable polymer.

The culture container prepared by using the mesh sheet may be not particularly limited, but be prepared in any shape, for example circular, oval, cone, or cylindrical shape, provided that the shape is suitable to hold microalgae.

In addition, a whole or part of the boundary surface of the culture container may be prepared with the mesh sheet, and others are prepared by using non-permeable or semipermeable and transparent or translucent material for maintaining a stereoscopic shape for floating. For example, when one end of a plastic container holding microalgae is sealed by using the mesh sheet, the container may be floated near the surface of seawater due to buoyancy of the plastic container.

A photobioreactor 102 illustrated in FIG. 2a of the present invention includes the culture container 110 illustrated in FIG. 1, and may further include a floating unit 120 in a tube shape extended from the culture container 110. The floating unit in a tube shape may be formed with a material the same as or different from a base material of the culture container. Preferably, the same material is used in consideration of a manufacturing process. According to an embodiment of a photobioreactor of the present invention, the floating unit in a tube shape may be formed by: introducing air to form a culture container in a balloon shape; and adhering boundaries thereof through heat-press. In that case, the culture container 110 parts are surrounded by the floating unit 120, and a whole or part of the culture container 110 may be substituted with the mesh sheet 111.

The floating unit may be a material such as typical Styrofoam, buoy, or empty vessel, and coupled to the culture container via a coupling unit (FIG. 5).

Figure 3A:
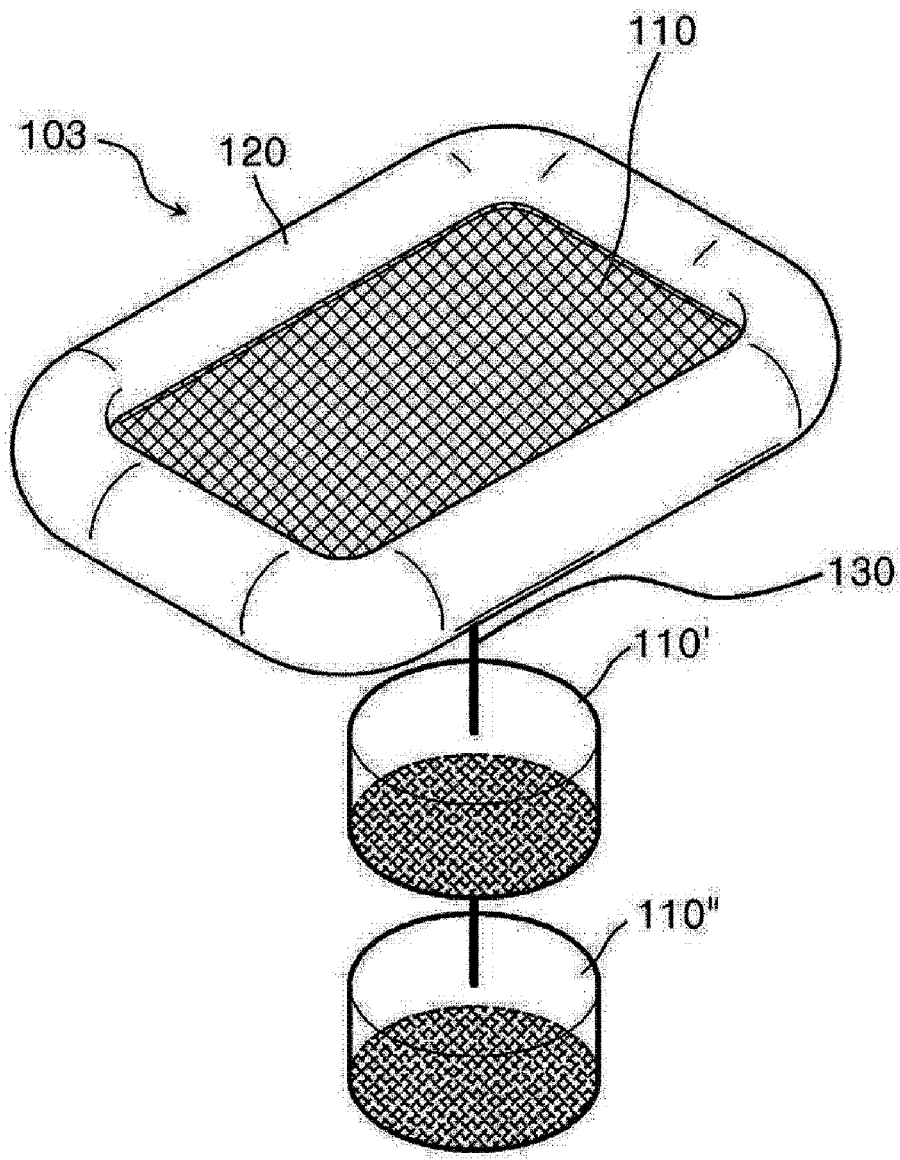
FIG. 3a is an illustrative drawing of vertically coupled culture containers.
Figure 3B:
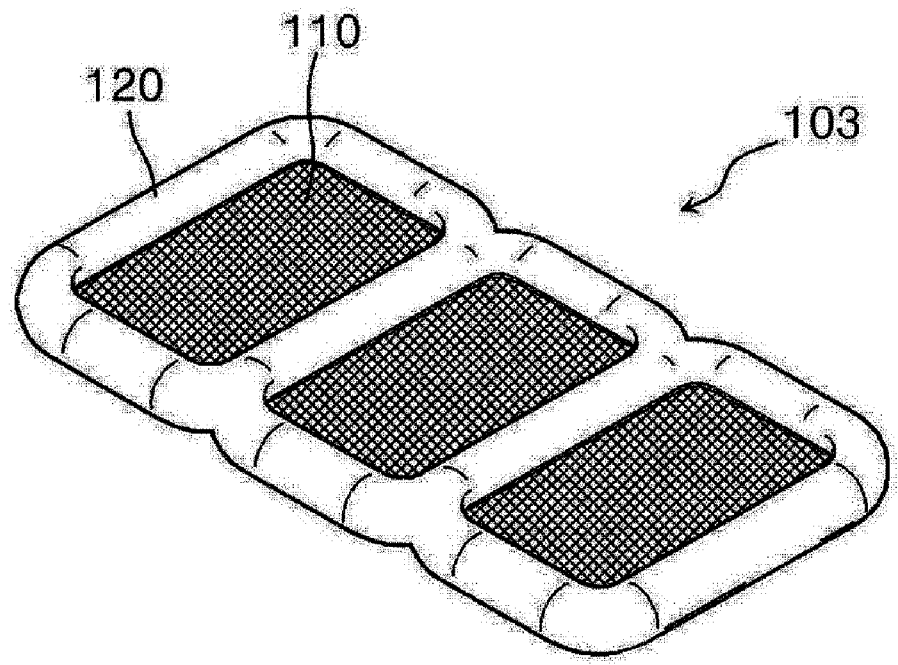
FIG. 3b is an illustrative drawing of culture containers coupled in a row with an intra-connected floating unit.
Figure 3C:
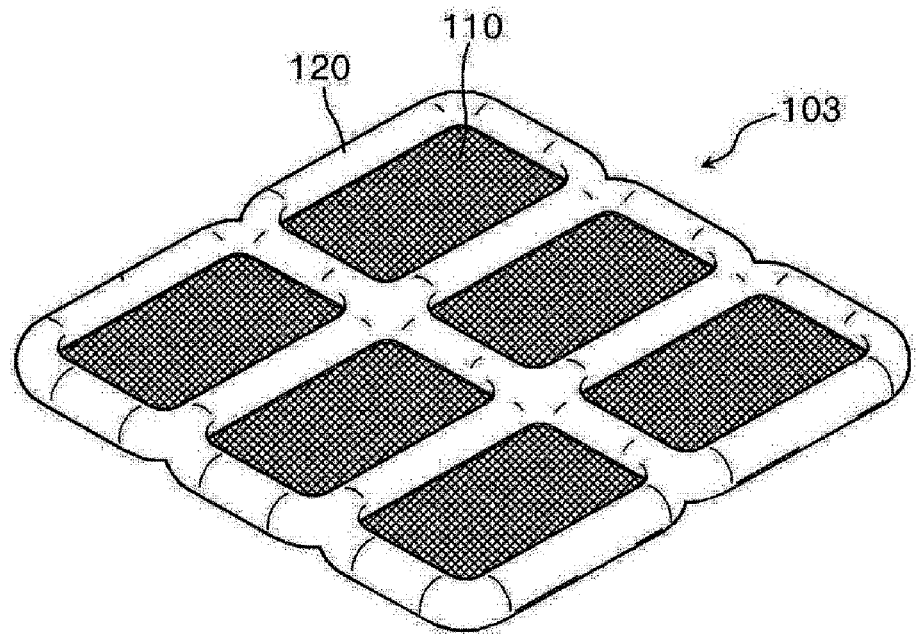
FIG. 3c is an illustrative drawing of culture containers in series-parallel with the intra-connected floating unit.
Figure 3D:
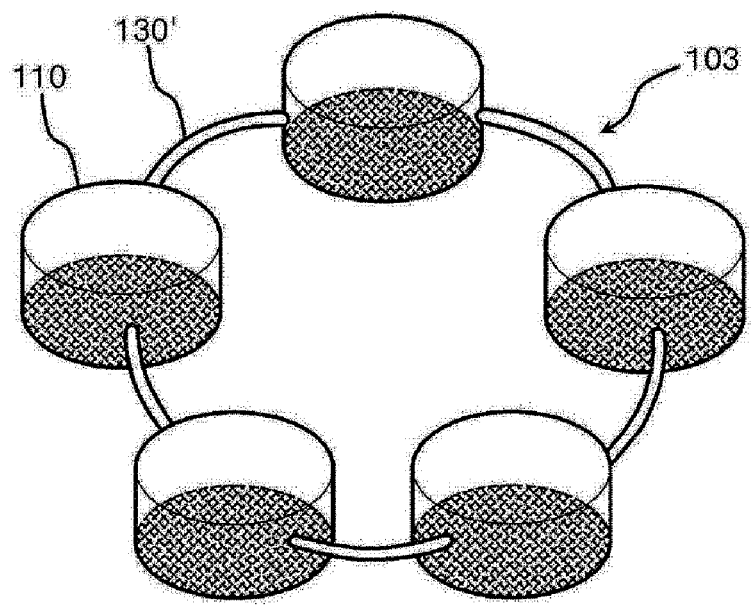
FIG. 3d is an illustrative drawing of culture containers coupled in a ring shape through floating type coupling units which interconnect the culture containers, without the intra-connected floating unit.
Figure 3E:
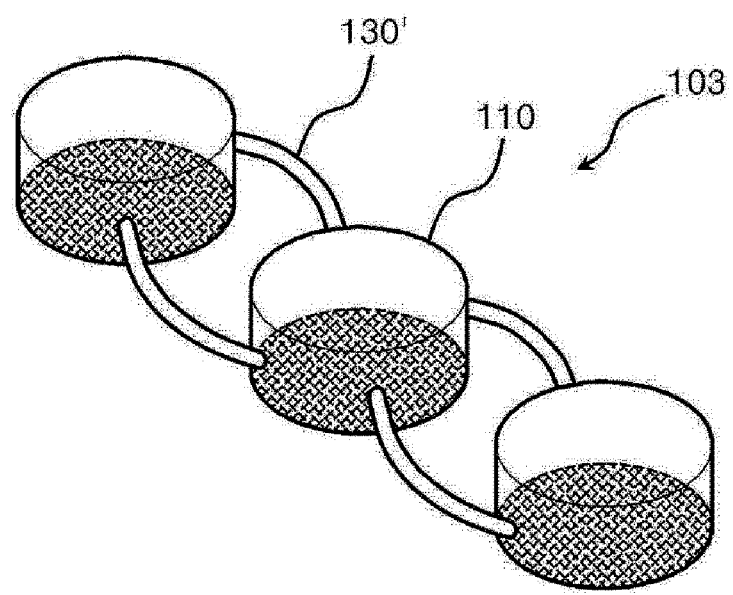
FIG. 3e is an illustrative drawing of culture containers coupled in a row through floating-type coupling units, without the intra-connected floating unit.

Photobioreactor 103 illustrated in FIGS. 3a to 3e of the present invention includes the culture container 110 illustrated in FIG. 1, and may further include one or more coupling units 130 coupled to the culture container 110. The coupling unit 130 may be anyone, regardless of shapes or materials, provided that the coupling unit is capable of coupling the culture containers according to an example of a photobioreactor illustrated in the drawings of the present invention each other or coupling and securing the culture container and the floating unit. For example, a ropes or chain may be used. The culture containers 110 may be vertically coupled. In that case, the floating unit 120 is only included in the uppermost culture container, and culture containers 110', 110" coupled downward to the uppermost culture container do not include the floating unit 120 (FIG. 3a). Optionally, the photobioreactor 103 according to an example of the present invention has a plurality of culture containers 110 which may be coupled in series (FIG. 3b) or in series-parallel (FIG. 3c) by an intra-connected floating unit 120 without a separate coupling unit. Optionally, as shown in FIGS. 3d and 3e, a plurality of culture containers 110 without a floating unit may be coupled in a circular shape (FIG. 3d) or in a row (FIG. 3e) by a floating-type coupling unit 130' which is prepared with a material capable of floating (e.g. buoy, styrofoam, or plastic vessel or tube having a vacuum inside or including air or gas therein capable of providing buoyancy) to be floated the culture containers 110 on the water surface. In that case, the culture container 110 may further include additional floating units (not shown). Types of coupling the culture containers may vary depending on types of microalgae to be cultured and marine environment where the culture containers are placed. For example, when one or more types of microalgae are cultured, the culture containers may be vertically coupled and then placed on sea. Additionally, when one type of microalgae is cultured, a floating-type coupling unit having adjusted buoyancy may be used to couple the containers from side to side or in a circular shape such that the containers are located within a range of depth of water where solar light required for culture of the microalgae to be cultured penetrates.

A photobioreactor 104 illustrated in FIG. 4 of the present invention includes the culture container 110 illustrated in FIG. 1, and may further include one or more sedimentation unit 140 coupled to the culture container 110 so that the culture container 110 is allowed to be submerged at an appropriate water depth. The sedimentation unit 140 may be a plumb bob, or a structure placed under the water surface or water.

Figure 2B:
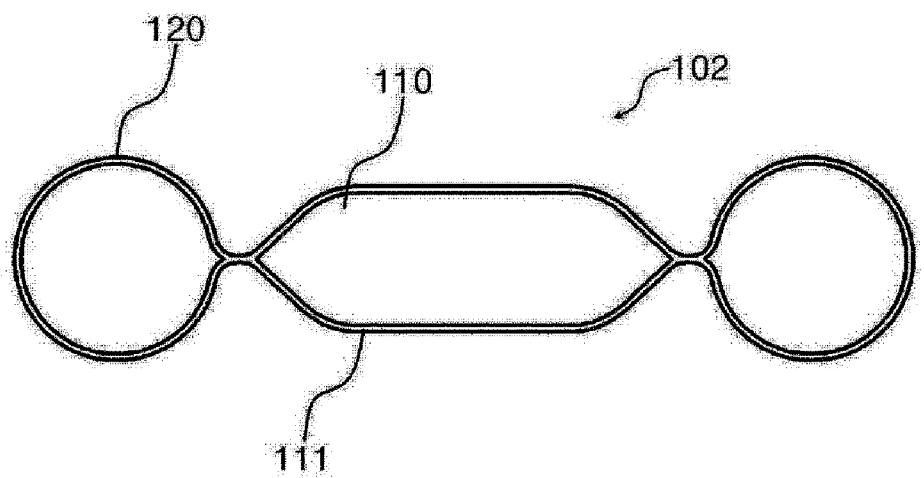

A photobioreactor 105 illustrated in FIG. 5 of the present invention includes the culture container 110 illustrated in FIG. 1, FIG. 2a or 2b, and may further include a floating unit 120 and a sedimentation unit 140 coupled to the culture container 110. For example, the floating unit 120 may be coupled to one end of the culture container 110 via a coupling unit 130, and the sedimentation unit 140 may be coupled to the other end of the culture container 110. Through the floating unit 120 and the sedimentation unit 140, degrees of floating and sedimentation of the culture container may be adjusted.

A photobioreactor 109 illustrated in FIG. 6a of the present invention may have an open-type culture container 110' having an open upper face. In that case, the culture container 110' may include an upper frame 113 and a boundary surface coupled thereto, wherein a part or whole of the boundary surface is prepared with a material 111 such as a mesh sheet or perforated sheet which allows gas, water, and nutrients to freely pass through, while restricting free pass of microalgae. The upper frame 113 may have any shape such as an oval, a circle, or a polygon, for example a rectangle or square, capable of forming a stereoscopic structure of the open-type culture container 110', and the boundary surface may be coupled to the upper frame 113 with a shape similar to a scoop net (not shown). Optionally, to maximize the volume of the open-type culture container 110' and stabilize the structure, vertical frames 114 coupled to the upper frame 113 and/or lower frame 115 may be additionally provided. Hereinafter, as shown in FIG. 6a, the open-type culture container 110' is described in more detail, wherein the culture container is provided with the rectangular upper frame 113, vertical frames 114 at four edge of the rectangle, lower frame 115 for coupling the vertical frames 114 each other, bottom wall 116 for coupling frames to frames, and four side walls 117 in all directions. A part or whole of the bottom wall 116 may be prepared with the material 111 such as a mesh sheet or perforated sheet which allows gas, water, and nutrients to freely pass through, while only restricting free pass of microalgae, and remaining parts may be prepared with a nonpermeable film material capable of substantially confining the microalgae. Optionally, the bottom wall 116 may be prepared with an nonpermeable film material and a part or whole of four side walls 117 may be prepared with the material 111 such as a mesh sheet or perforated sheet which allows gas, water, and nutrients to freely pass through, while only restricting free pass of microalgae, or both of the bottom wall 116 and four side walls 117 may be prepared with the material 111 such as a mesh sheet or perforated sheet which allows gas, water, and nutrients to freely pass through, while restricting only free pass of microalgae. The open-type culture container 110' having such structure, however, may have difficulty in floating onto the water surface, and thus a part or whole of the upper frame 113 may be provide with a separate floating unit 120. Optionally, the open-type culture container 110' may have a structure in which the upper frame itself 113 is prepared with a buoyant material or the upper frame 113 is directly and indirectly coupled to the floating unit 120. In the former case, the upper frame 113 of the culture container 110' may be prepared with one or more tube into which air is introduced, or an empty plastic frame. In the latter case, a floating unit (e.g. styrofoam, or a plastic vessel having a vacuum inside or including air or gas capable of providing buoyancy) may be attached to the side or lower part of the upper frame 113. A workbench may be added to the upper frame 113 to facilitate a process of inoculation or recover of microalgae by an operator. Optionally, the workbench may be omitted in the case where the upper frame itself 113 directly plays a role as a floating unit or the upper frame 113 is overlaid with the floating unit 120. As necessary, the upper frame 113 may house the bottom wall 116 or four side walls 117 to adjust the depth of the culture container 110'. In other word, the upper frame 113 may house the bottom wall 116 or four side walls 117 under cloudy weather or season of weak solar light such that the depth of the culture container 110' may become smaller, whereas the bottom wall 116 or four side walls 117 protrude from the upper frame 113 under sunny weather or season of strong solar light such that the depth of the culture container 110' may become greater.

Moreover, a photobioreactor 209 illustrated in FIG. 6b of the present invention may include an open-type culture container having a raceway pond 210 placed to be floated on the water surface. In that case, as shown in FIG. 6b, a partition 218 may be placed on the middle of the open-type culture container having a raceway pond 210 such that the culture container has a structure in which a culture solution may be rotated in one direction. In that case, for smooth rotation of the culture solution, a culture solution circulator 219 such as a waterwheel or pump may additionally be included. Basically, the culture solution circulator 219 may be rotated by wind or wave, and additionally be provided with a motor supplying rotational force by a separate power such as batteries or photovoltaic power generators for continuous rotation in one direction (not shown). A basic structure of the open-type culture container having a raceway pond 210 is similar to that of the open-type culture container 110' illustrated in FIG. 6a. The open-type culture container having a raceway pond 210 may include an upper frame 213, and a boundary surface coupled to the upper frame 213, wherein the upper frame may be formed in an oval, longitudinally elongated oval, or circular shape. To maximize the volume of the open-type culture container having a raceway pond 210 and stabilize the structure, the container may further be provided with vertical frames 214 coupled to the upper frame 213 and/or a lower frame 215. Hereinafter, as shown in FIG. 6b, the open-type culture container having a raceway pond 210 is described in more detail, wherein the culture container includes the upper frame 213 in a longitudinally elongated oval shape, vertical frames 214 coupled downward to the oval-shaped upper frame 213, the lower frame 215 coupling the vertical frames 214 each other, side walls 217 and bottom wall 216 for coupling the frame to frame. A part or whole of the bottom wall 216 may be prepared with a material 211 such as a mesh sheet or perforated sheet which allows gas, water, and nutrients to freely pass through, while only restricting free pass of microalgae, and remaining parts may be prepared with a nonpermeable film material capable of substantially confining microalgae. Optionally, the bottom wall 216 may be prepared with nonpermeable film material and a part or whole of side walls 217 may be prepared with the material 211 such as a mesh sheet or perforated sheet which allows gas, water, and nutrients to freely pass through, while only restricting free pass of microalgae, or both of bottom wall 216 and side walls 217 may be prepared with the material 211 such as a mesh sheet or perforated sheet which allows gas, water, and nutrients to freely pass through, while only restricting free pass of microalgae. The open-type culture container having a raceway pond 210 having such structure, however, may have a difficulty in floating onto the water surface, and thus a part or whole of the upper frame 213 may be provide with a separate floating unit 220. Optionally, the open-type culture container having a raceway pond 210 may have a structure in which the upper frame itself 213 is prepared with a buoyant material or the upper frame 213 is directly covered with the floating unit 220. In the former case, the upper frame 213 of the culture container having a raceway pond 210 may be prepared with one or more tube into which air is introduced or an empty plastic frame. A workbench may be added to the upper frame 213 to facilitate a process of inoculation or recover of microalgae by an operator. Optionally, the workbench may be omitted in the case where the upper frame itself 213 directly plays a role as the floating unit, or the upper frame 213 is covered with the floating unit 220.

As above, when the culture container having the open upper part, and the side and/or bottom face a whole or part of which has the boundary surface allowing gas, water, and nutrients to freely pass through, while restricting free pass of microalgae is used, it is possible to more efficiently culture microalgae because the raw cost is greatly reduced; gases are more freely exchanged; wastes generated during the photosynthetic process are readily removed; and nutrients are readily supplied from environmental water.

A photobioreactor 107 illustrated in FIG. 7 of the present invention includes the culture container 110 illustrated in FIG. 1, and may further include a light blocking area 160 in one end of the culture container 110. For example, by including the light blocking area 160 in one end of the culture container 110, the photobioreactor is configured to adjust wavelengths or amount of light energy delivered to microalgae to be cultured, wherein the light blocking area may be included in the culture container in a shape such as a pattern.

Figure 8B:
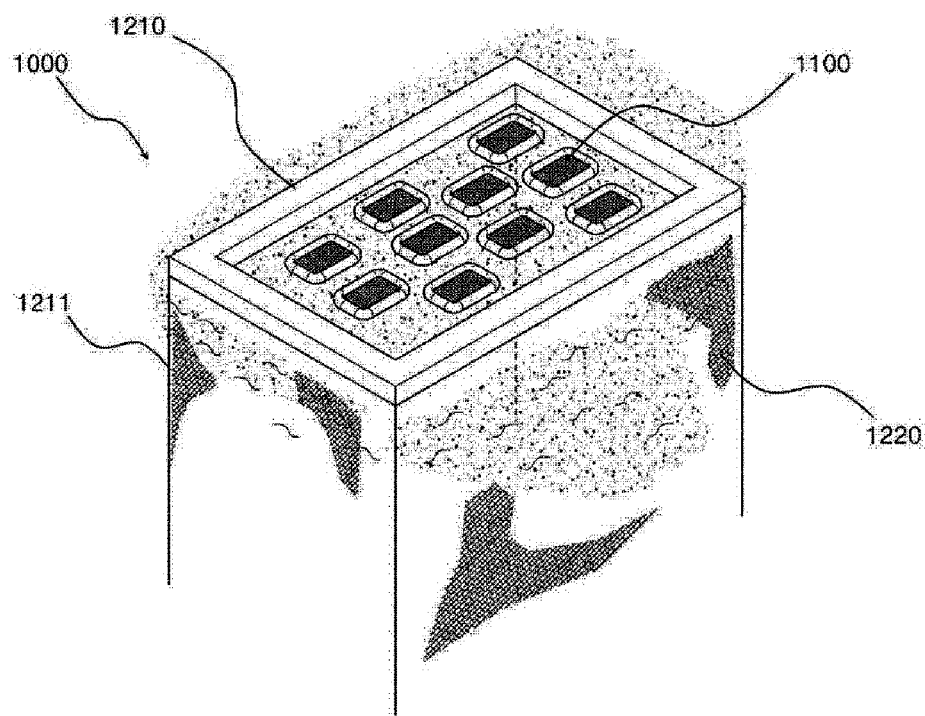
FIG. 8b is an illustrative drawing of a microalgae culturing field having a plurality of photobioreactors with a floating unit.

A microalgae culturing field 1000 illustrated in FIG. 8 of the present invention may include a photobioreactor 1100 and a floating structure 1200 holding the photobioreactor, wherein, in the culturing field, a plurality of culture containers capable of culturing microalgae are secured at a certain location of the water surface to facilitate recover after the culture without loss. To prevent loss of the photobioreactor 1100, the floating structure 1200 includes a culturing field upper frame 1210 and fences 1220 for coupling the culturing field upper frame 1210 to frame to separate inside and outside of the culturing field 1000. In addition to the culturing filed upper frame 1210 floated on the water surface, the microalgae culturing field 1000 illustrated in FIG. 8a of the present invention may further include culturing filed vertical frames 2011 and a culturing field lower frame of 1212 which submerge under the water surface, wherein the culturing field upper frame 1210 may have any shape such as an oval, circle, or polygonal, for example rectangle, or square, capable of stereoscopically forming a culture container 1110, and in the case where fences 1220 are coupled to the culturing filed upper frame 1210 like a scoop net (not shown), the culturing field vertical frame 1211 and the culturing filed lower frame 1212 may be omitted. The fences 1220 may be prepared with various materials such as plastics, wood, plywood, or nets, but preferably be prepared with nets in terms of costs and free communication of environmental water. The microalgae culturing field 1000 thus formed has a structure similar to a sort of floating fish cages. The culturing field upper frame 1210 of the floating structure 1200 on the water surface may be provided with a culturing field floating unit 1213 to be floated the floating structure 1200 onto the water surface. The culturing filed floating structure 1213 may adjust buoyancy taken into account conditions such as solar light energy and nutritional salts required for culture of microalgae to be cultured. The culturing field floating unit 1213 may be prepared with various materials such as styrofoam, and an empty plastic vessel, and may overlay the culturing field upper frame 1210 or be coupled to the culturing field upper frame 1210 via a separate coupling unit. In addition, the floating structure 1200 may be configured to include an operator supporting unit (not shown) allowing an operator to conduct a management work. The operator supporting unit plays a role as a support on which an operator may conduct a work, and also the operator supporting unit may be coupled to the culturing field floating unit 1213 or to an underwater or floating facility separated from the culturing filed floating unit 1213 (not shown). The operator supporting unit itself may be prepared with a buoyant material, thereby replacing the culturing filed floating unit 1213. Namely, when the supporting unit (not shown) prepared with a buoyant material overlays the culturing filed upper frame 1210, the culturing filed floating unit 1213 may be omitted. As shown in FIG. 8b, when the culturing field upper frame 1210 is prepared with a buoyant material (e.g. tube or empty plastic frame), the culturing filed floating unit 1213 and operator supporting unit may be omitted. The photobioreactor 1000 may be provided with or without a floating unit. When the photobioreactor 1000 is not provided with a floating unit, the depth of the bottom face 1221 of the floating structure 1200 may be adjusted to prevent the photobioreactor 1100 from submerging under the water surface too deep. Merely, when the photobioreactor 1100 is provided with a floating unit, as shown in FIG. 8b, the bottom face 1221 and culturing field lower frame 1212 of the floating structure 1200 may be omitted.

As above, when culture is performed by confining the photobioreactor according to the present invention by using the microalgae culturing filed, it is possible to prevent loss of the photobioreactor without a particular securer, and to facilitate drop and recover of the photobioreactor.

Figure 9A:
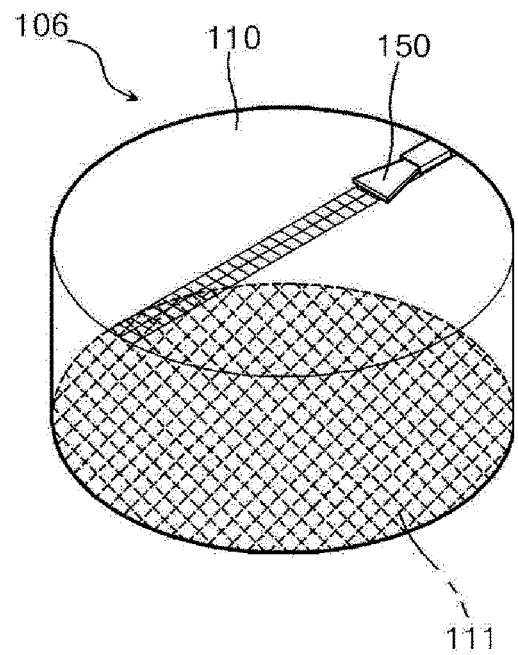
FIG. 9a is an illustrative drawing of a zipper-type opening and shutting unit which may be coupled with an inlet and outlet of a photobioreactor.
Figure 9B:
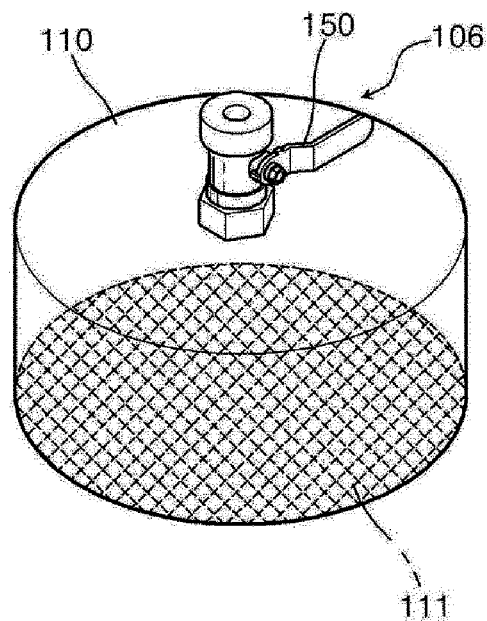
FIG. 9b is a valve-type opening and shutting unit which may be coupled with an inlet and outlet of a photobioreactor.

Photobioreactors 106 illustrated in FIGS. 9a and 9b of the present invention includes the culture container 110 illustrated in FIG. 1, and may further include an opening and shutting unit 150 coupled to the culture container 110. For example, the switching unit 150 is included in one end of the culture container 110 to allow the culture container 110 to hold microalgae, wherein the switching unit may have a shape such as a zipper (FIG. 9a), a zipper bag or a valve (FIG. 9b) to facilitate opening and shutting.

Figure 10A:
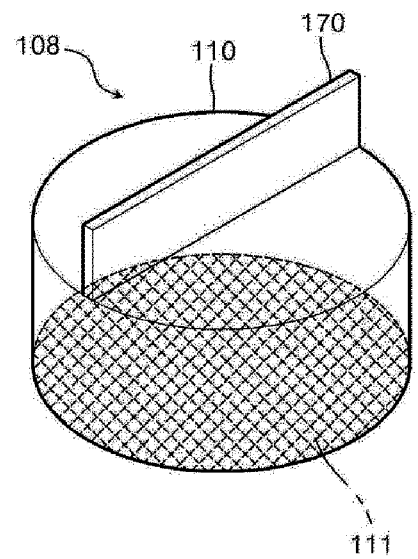
FIG. 10a is an illustrative drawing of a fan structure extended to the direction different from each other coupled to a photobioreactor.
Figure 10B:
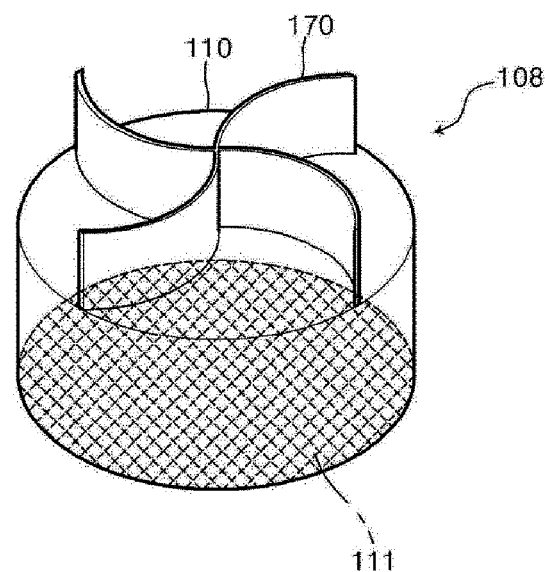
FIG. 10b is an illustrative drawing of a curve-type fan structure coupled to a photobioreactor.
Figure 10C:
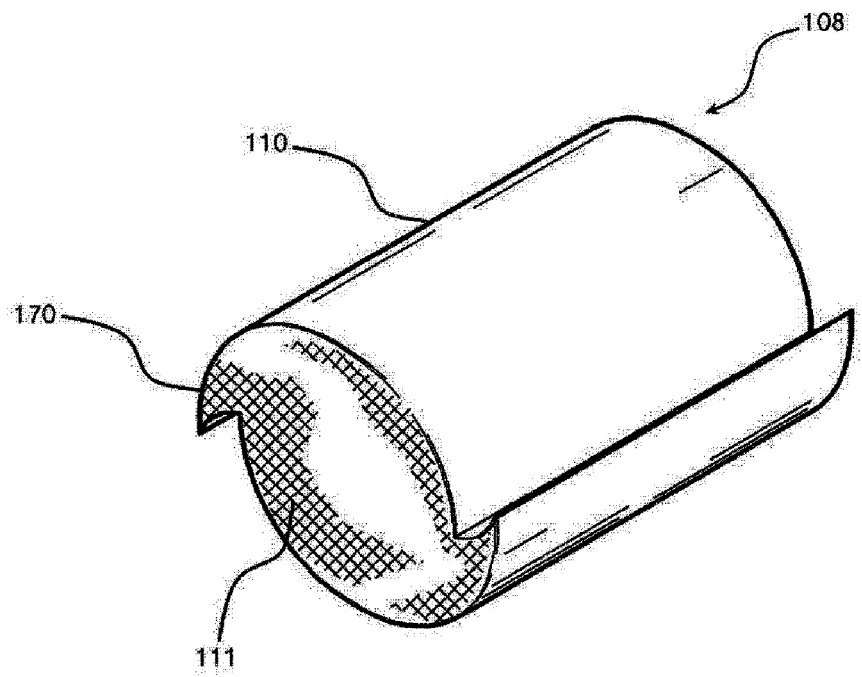
FIG. 10c is an illustrative drawing of a fan structure in which both sides of the culture container are elongated like pinwheel.
Figure 10D:
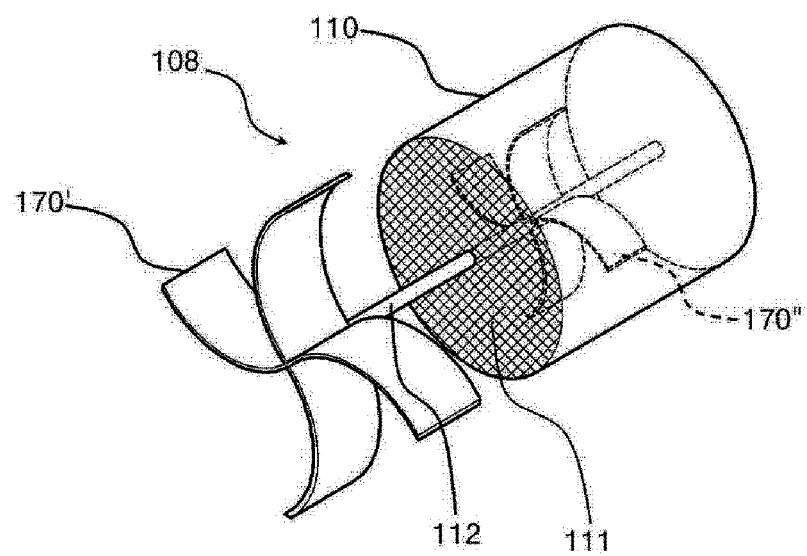
FIG. 10d is an illustrative drawing a fan structure having an axis penetrating the culture container and an exterior rotary fan and an interior rotary fan.

Photobioreactors 108 illustrated in FIGS. 10a to 10d of the present invention is characterized by having a wobbling structure allowing a culture container 110 to wobble by wind or wave. For example, as shown in FIG. 10a, the culture container 110 illustrated in FIG. 1 is included, and a fan 170 coupled to the culture container in a wobbling structure may further be included. The fan 170 is configured to attach a lower or upper face of the culture container to allow the culture container to be rotated in a vertical direction by a force caused by wind or water. One or two crossing fans 70 may be attached to the lower or upper face of the culture container. Also, as shown in FIG. 10b, the fan may be configured in a curved shape to broaden a cross section where wind is reached to facilitate rotation. Moreover, the wobbling structure may be applied to a shape of the culture container itself 110. For example, as shown in FIG. 10c, both sides of the culture container 110 are elongated, thereby forming the fan 170 similar to a pinwheel, such that the culture container 110 is capable of wobbling by wind or wave. In that case, for efficient wobbling of the culture container 110, both protruded fans 170 are preferably directed in an angle of 180 degrees from each other. Optionally, the wobbling structure may include an outer rotary fan 170', which is attached to an axis 112 penetrating the culture container and rotated by wind or wave, and an inner rotary fan 170" which is interlocked to the outer rotary fan 170' and rotated inside of the culture container (FIG. 10d). A shape of the outer rotary fan 170' may be any structure such as pinwheels, propellers, or waterwheels, provided that the structure is capable of being rotated by wind or flow of water.

Hereinafter, the present invention will be described in more detail with reference to examples. However, the following examples are only to illustrate the present invention, and the scope of the present invention is not limited thereto.

EXAMPLES

Figure 11:
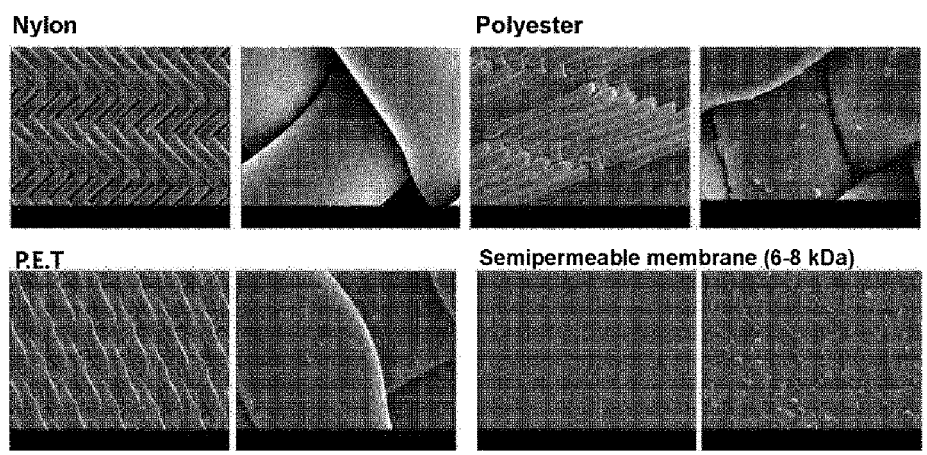
FIG. 11 is a series of scanning electron microscope images of mesh sheets according to examples of the photobioreactor illustrated in the present invention.

Example 1: Measurement of Microalgae Permeability of Photobioreactor Prepared with Mesh Sheet An experiment was conducted to investigate whether microalgae are released through a mesh sheet. Culture containers were constructed by attaching mesh sheets respectively prepared with PET, polyester and nylon to bottoms of plastic containers having a total volume of 100 ml. 60 ml of microalgae (wet weight: 0.5 g/l) (*Tetraselmis* sp.) was placed into the culture container and the container was allowed to be floated on a plastic container containing 1 l of f/2-Si medium to investigate whether the microalgae were released to the outside of the culture containers prepared with the mesh sheets. A mesh size for nylon and PET was 5 μm, and a mesh size for polyester was 15 μm. If microalgae are released to the outside of the mesh sheet, the microalgae would grow using a medium at the outside. During the culture of microalgae, temperature was maintained at 20° C., and 100 μE/m$^2$/s of intensity of light was supplied using fluorescent light. After five days of culture, concentrations of microalgae at the inside and outside of the reactor were measured with coulter counter (model: multisizer 3, Beckman Inc., USA). FIG. 11 shows scanning electron microscopy results of nylon, polyester, and PET mesh sheets and a semipermeable membrane having a molecular weight cut-off value of 6-8 kDa used in the experiment.

Characterization of the mesh sheet used and volume of culture solution contained in the culture container set forth in Table 1 below.

Figure 12:
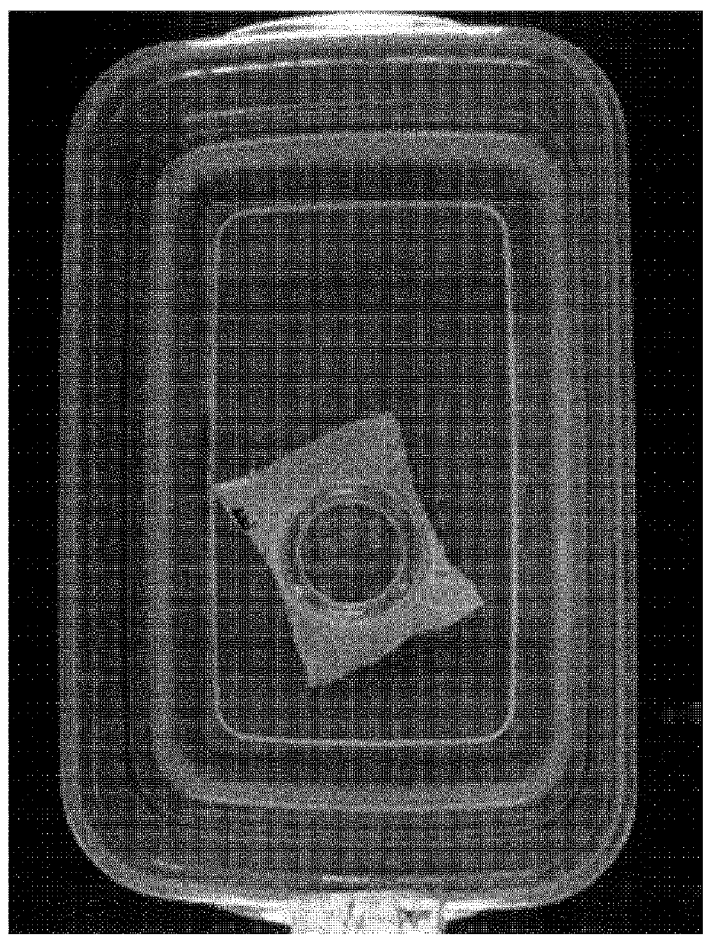
FIG. 12 is an image showing an experimental process to evaluate whether microalgae are released from a photobioreactor according to an example of the present invention.
Figure 13:
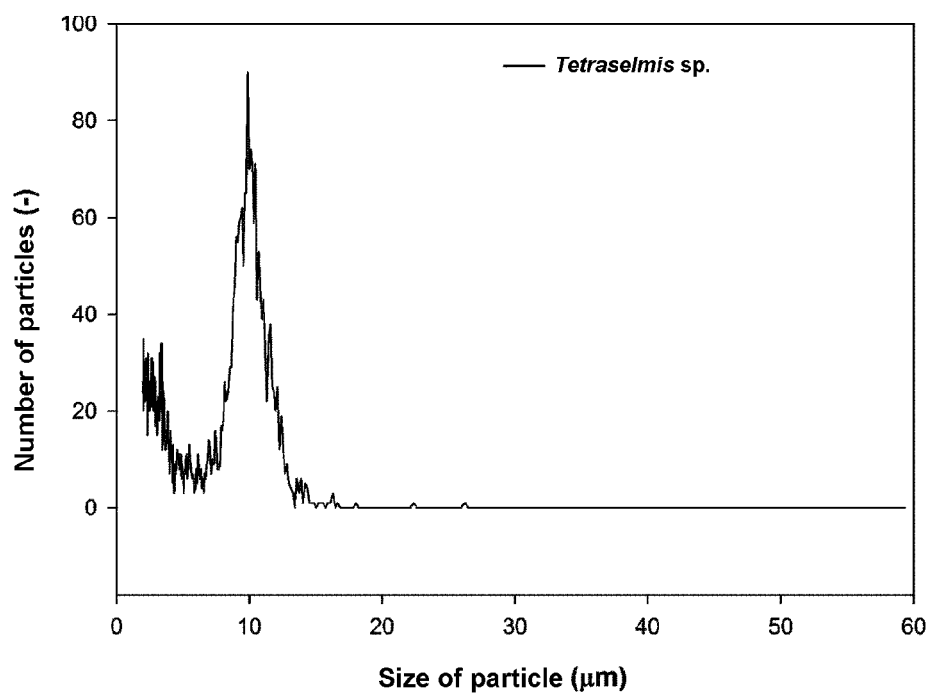
FIG. 13 is a graph obtained by analyzing the number of particles and sizes of cell particles in a culture container to evaluate whether microalgae are released to the outside of the culture container of a photobioreactor according to an example of the present invention.
Figure 14:
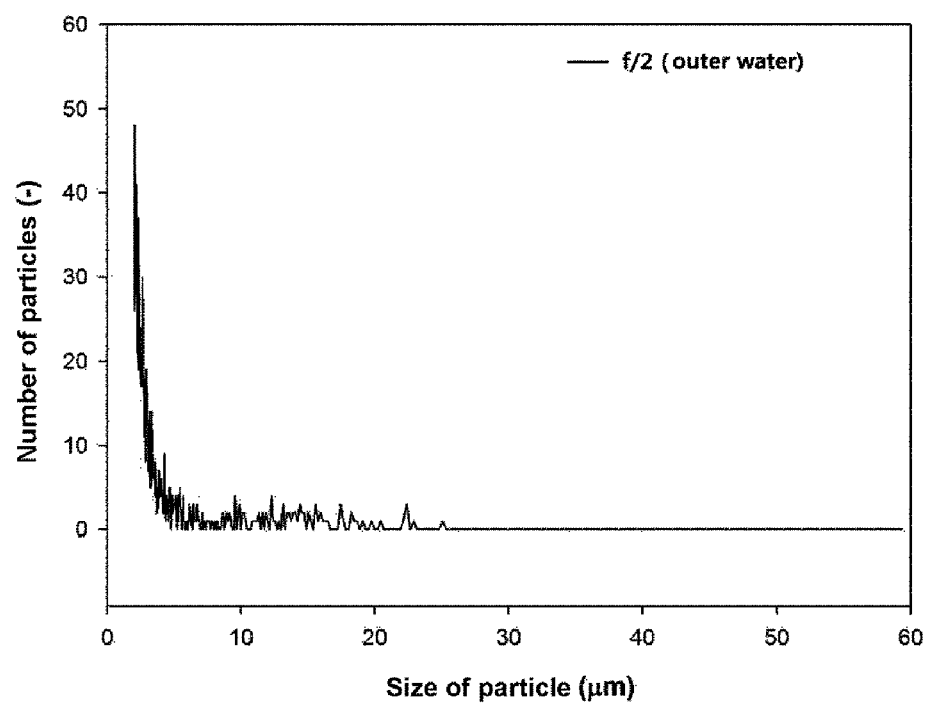
FIG. 14 is a graph obtained by analyzing the number of particles and sizes of cell particles in an outer water bath holding a culture container after culturing cells for a certain period of time to evaluate whether microalgae are released to the outside of the culture container of a photobioreactor according to an example of the present invention.

As shown in FIG. 12, one face of the plastic container was sealed with the mesh sheet using PET, and microalgae were introduced into the container and cultured to investigate whether the microalgae are released or not. Consequently, it can be found that cell size and dispersity of the microalgae in the culture container were exhibited as shown in FIG. 13, and that microalgae having an average size of about 11 μm were dispersed in the culture container. Also, as shown in FIG. 14, it can be found that although cells having a size of about 5 μm or less were observed at the outside of the culture container, cultured microalgae were not released from the culture container (FIGS. 13 and 14).

TABLE 1

|  | Length (m) | Width (m) | Surface area (m$^2$) | Thickness (m) | Culture solution volume (m$^3$) |
|---|---|---|---|---|---|
| Nylon | 0.065 | 0.045 | 0.002925 | 0.000100 | 0.00006 |
| Polyester) | 0.065 | 0.045 | 0.002925 | 0.000065 | 0.00006 |
| PET | 0.065 | 0.045 | 0.002925 | 0.000033 | 0.00006 |

Example 2: Measurement of Growth Level of Microalgae Using Photobioreactor Prepared with Mesh Sheet Microalgae were cultured by practically using the culture container prepared with the mesh sheet, and also microalgae were cultured by using a semipermeable membrane of a cellulose material as a control.

1 l of f/2-Si, and 1 l of natural seawater (NSW) were poured into two plastic water baths having a capacity of containing 2 l of an aqueous solution, wherein the NSW was prepared by diluting f/2 medium to 1/30 in order to adjust nitrogen and phosphorus concentration similar to that of dissolved in seawater of Incheon. The mesh sheet with polyester or nylon material (0.003 m$^2$) was attached to the bottom of the plastic reactor. 100 ml of culture medium, to which 0.05 g/l (wet weight) of microalgae were inoculated, was poured into the plastic container, and then the container was allowed to be floated on the water bath and microalgae were cultured (FIG. 15). As a control, the same width of a semipermeable membrane of a cellulose material having 50 kDa of molecular weight cut-off (product number 132544, spectrumlabs, USA) was attached, and then experiment was conducted to compare growth rates of microalgae. To maintain a concentration difference of nutritional salts between the inside and outside of the culture container consistent, the medium was periodically replaced once a day. 100 μE/m$^2$/s of light was supplied for 24 hours by using fluorescent light during the culture. The culture temperature was maintained at 20° C. Culture was continued for 18 days. On 0, 3, 6, 9, 12, 15 and 18 days after the culture, 1-2 ml of culture solution was taken through a sampling port placed on the upper part of the culture container to measure growth rate of cells and nitrogen concentration of the culture solution.

Figure 16:
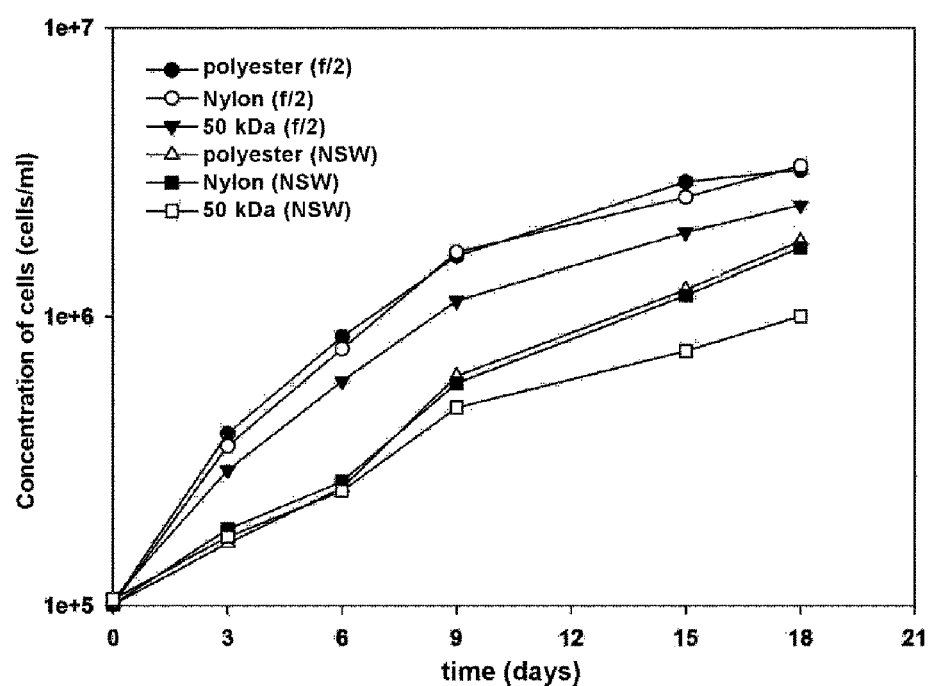
FIG. 16 is a graph comparing growth rates of microalgae depending on types of the mesh sheet and semipermeable membrane used in preparation of a photobioreactor according to an example of the present invention.

Consequently, as shown in FIG. 16, it can be found that, irrespective of types of medium, growth of microalgae was better when polyester or nylon mesh sheet was used than the case where the cellulose semipermeable membrane, i.e. the control, was used. Particularly, it has been shown that, in wet weight of microalgae, the growth rates were higher by about 25% (for microalgae cultured in f/2) and by about 60-80% (for microalgae in the water bath containing near seawater) with respect to that of microalgae for the case where 50 kDa cellulose semipermeable membrane, i.e. the control was used (FIG. 16). These results demonstrate that nutritional salts in the outside of the culture container have high permeability to the mesh sheet than the semipermeable membrane, and thus the mesh sheet may facilitate growth of microalgae.

Example 3: Measurement of Salt Permeability of Photobioreactor Prepared with Mesh Sheet In the present example, nutritional salt permeability was measured in the culture container prepared with the mesh sheet. For the control, a semipermeable membrane of a cellulose material was used to culture microalgae.

Nutritional salts permeability was measured with a transfer rate of nitrates, which is an important factor for culture of microalgae. A method for measuring nutritional salt permeability of the mesh sheet was as follows: 2 l of seawater including nitrates having concentrations of 100, 200 or 400 mg/l was prepared in a rectangular water bath; a rectangular plastic container containing 100 ml of seawater without nitrates was allowed to be floated on the water bath; and changes in the concentration difference due to introduction of nitrates from the water bath to the plastic container was measured with lapse of time.

Consequently, as shown in Table 2 below and FIG. 17, it can be found that the nitrate component penetrates into the culture container through the mesh sheets with nylon, polyester, or PET material about 30 times more easier than the cellulose semipermeable membrane. Such trend was not equally exhibited for the semipermeable membrane. For the semipermeable membrane, even in the case where molecular weight cut-off was increased to 3.5 kDa, 6-8 kDa, 15 kDa and 50 kDa, amounts of penetration were not increased, and the maximum value was merely about 1/28 of that of the mesh sheet. These results demonstrate that there is limitation in directly culturing microalgae in environmental water by using the semipermeable membrane alone, and that the culture container prepared with the mesh sheet according to the present example may provide microalgae with nutritional salts required for growth without release of the microalgae, thereby efficiently increasing productivity of microalgae.

TABLE 2

|  | $NO_3^-$ transfer rate (mg/l/min) | timated Max. $NO_3^-$ transfer rate (mg/m$^2$/day) | timated Max. $NO_3^-$ transfer rate (g/m$^2$/day) |
|---|---|---|---|
| 3.5 kDa Semipermeable membrane | 0.0291 | 154 | 0.154 |
| 6~8 kDa Semipermeable membrane | 0.0257 | 136 | 0.136 |
| 15 kDa Semipermeable membrane | 0.0325 | 172 | 0.172 |
| 50 kDa Semipermeable membrane | 0.0352 | 187 | 0.187 |
| Nylon mesh sheet | 0.1866 | 5512 | 5.512 |
| Polyester mesh sheet | 0.1869 | 5522 | 5.522 |
| P.E.T mesh sheet | 0.1835 | 5420 | 5.420 |

Example 4: Measurement of Growth Rate of Microalgae Using Photobioreactor Prepared with Mesh Sheet for Marine Culture The present inventors placed the photobioreactor according to an embodiment of the present invention on a marine culturing filed in Yeongheung-Do. Then, *Tetraselmis* sp.

(KCTC12236BP) was cultured for 9 days to investigate growth of the strain and penetration degrees of a nitrogen source. The same type of microalgae were cultured in photobioreactors prepared by using non-permeable membrane (polyethylene) and semipermeable membrane together with the reactor prepared with the mesh sheet according to the present example. The photobioreactor had a structure as shown in FIG. 18. A plastic container as described in FIG. 19 was used. The mesh sheet, non-permeable or semipermeable membrane was applied to the bottom for comparison. Microalgae were introduced into the culture container (FIGS. 18 and 19). Specifically, for the non-permeable membrane, polyethylene was used, and, for the mesh sheet, PET, nylon, or polyester was used. Culture was performed by adding three times of f/2-Si medium and 4 g/l of sodium bicarbonate for supply of carbon source. As the semipermeable membrane (SPM), semipermeable membranes with a cellulose material having molecular weight cut-off of 6-8 kDa and 15 kDa (product number 132544, spectrumlabs, USA) were used (FIG. 20).

During culturing *Tetraselmis* sp. for 9 days, temperature, water temperature, measured water temperature, and measured temperature of the marine culturing field at Yeongheung-Do were shown in FIG. 21. A day of initiating culture of microalgae was determined as time 0. In addition, daily photosynthetically active radiation (PAR) and time of light irradiation during culture were summarized in FIGS. 22a and b. During culture of microalgae, average water temperature was 9.9° C.; average atmosphere temperature was 4.2° C.; average PAR was 295.5 $\mu E/m^2/s$; and average light irradiation time was 7.4 hours (FIGS. 21, 22a and 22b). Growth rate of microalgae in the photobioreactor was determined based on cell concentration and wet weight of microalgae. When the photobioreactor prepared by using the mesh sheet of polyester or PET material were used, growth rates of microalgae were respectively increased to $1.68 \times 10^6$, and $1.77 \times 10^6$ cells/ml (FIG. 23a). Also, when the mesh sheet of polyester or PET material was used, wet weights were increased by 1.14-1.48 times of that of the semipermeable membrane of 15 kDa was used (FIG. 23b). Interestingly, the semipermeable membrane having a low cut-off value of 6-8 kDa showed the lowest value which was lower than that of the control in which nonpermeable membrane was used (Table 3).

TABLE 3

| Day 9 | Control | Polyester | P.E.T | 6~8 kDa | 15 kDa |
|---|---|---|---|---|---|
| Wet weight (g/l) | 0.79 | 0.78 | 0.81 | 0.55 | 0.71 |
| Cell Concentration (cells/ml) | 1.70E+06 | 1.68E+06 | 1.77E+06 | 1.29E+06 | 1.60E+06 |

Example 5: Measurement of Reuse Efficiency of Culture Container Prepared with Mesh Sheet To investigate reuse efficiency of the mesh sheet according to the present example, the mesh sheet used in Example 4 was collected. The mesh sheet was, then, washed or not washed and used to culture *Tetraselmis* sp. strain for 9 days in a marine culturing device at Yeongheung-Do, while measuring nitrate transfer efficiency. As a control, the semipermeable membranes of a cellulose material having molecular weight cut-off of 6-8 kDa and 15 kDa, which were used in Example 4, were used after washing or without washing. Also, an unused membrane was used as a control for the whole experiment. Specifically, washing was performed with running tap water as follows: each used membrane was immersed in a 2 l of water bath filled with 1 l of tap water for about five minutes; and the front and reverse sides of the membrane were manually washed with running tap water for about 1 minute without an additional washing tool.

While culturing the *Tetraselmis* sp. strain for 9 days, transfer rates of nitrates through the membranes were compared through the same method as Example 3. Consequently, as shown in FIG. 24, nitrate penetration efficiency of the photobioreactors prepared with reused polyester and PET mesh sheets was better relative to that of the semipermeable membrane, and also penetration efficiency was increased by simply washing the sheet with tap water without an additional process. These results indicates that the mesh sheet according to the present invention may be reused after passing through a simple washing process with tap water, thereby having excellent industrial availability.

Example 6: Experiment of Culturing Microalgae *Dunaliella tertiolecta* Using Photobioreactor Prepared with Mesh Sheet and Artificial Seawater An experiment of culturing microalgae *Dunaliella tertiolecta* in artificially prepared seawater was performed to demonstrate that supply of environmental water increase growth rate of microalgae. A culture container was constructed by attaching a mesh sheet prepared with polyester to the bottom of a plastic container having a total volume of 200 ml. 150 ml of *Dunaliella tertiolecta* (wet weight of 0.03 g/l) was placed in the culture container, and the culture container was allowed to be floated on an acryl water bath containing 25 l of artificial seawater. For the experimental group of the present example, 1 l per day of artificial seawater was introduced through a solution quantity regulator, while the control was allowed to be floated without additional supply of artificial seawater such that nutrients were provided only through diffusion. To maintain nutrients in artificial seawater consistent, 25 l of artificial seawater was replaced once a day. During the culture, 200 $\mu E/m^2/s$ of light was supplied by using a fluorescent light for 24 hours, and culturing temperature was maintained at 20° C. Growth of microalgae was checked by measuring the volume of culture solution and cell wet weight in the culture solution daily. Consequently, when 1 l of artificial seawater (environmental water) was supplied daily, an average microalgae production for 0-10 days of culture was increased by 94% (from 0.083 g/l/day for the case where environmental water was not supplied to 0.16 g/l/day for the case where environmental water of 1 l/day was supplied) (FIG. 26).

Example 7: Experiment of Culturing Microalgae *Tetraselmis* Sp. KCTC12236BP Using Natural Seawater To demonstrate that the result obtained through above experiment was available to be applied to natural seawater as well as artificial seawater and also universally applied to microalgae, a culturing experiment was conducted by using natural seawater from Incheon sea and other types of microalgae, *Tetraselmis* sp. A culture container was constructed by attaching a mesh sheet prepared with polyester to the bottom of a plastic container having a total volume of 200 mL 150 ml of *Tetraselmis* (wet weight of 0.08 g/l) was placed in the culture container, and the culture container was allowed to be floated on an acryl water bath containing 60 l of natural seawater. For the present example, 1 l per day of natural seawater was introduced through a solution quantity regulator, while the control was allowed to be floated without additional supply of natural seawater such that nutrients were provided only through diffusion. To maintain nutrients in natural seawater consistent, 60 l of natural seawater was replaced once a day. During the culture, 200 µE/m²/s of light was supplied by using a fluorescent light for 24 hours, and culturing temperature was maintained at 20° C. Growth of microalgae was checked by measuring the volume of culture solution and cell wet weight in the culture solution daily. Consequently, as shown in FIG. 27, when 1 l of natural seawater (environmental water) was supplied daily, an average microalgae production for 0-6 days of culture was increased by 122% (from 0.025 g/l/day for the case where environmental water was not supplied to 0.056 g/l/day for the case where environmental water of 1 l/day was supplied). Therefore, it has been demonstrated that microalgae may be cultured by using natural seawater not artificially prepared seawater, and microalgae productivity may be increased by forced supply of environmental water.

Example 8: Experiment of Culturing *Tetraselmis* Sp. KCTC12236BP Depending on Regulation of Natural Seawater Supply To demonstrate that productivity of microalgae was increased as supply of environmental water increases, a culturing experiment was conducted by increasing environmental water supply to 1, 2, or 3 l/day under the same condition as Example 7. A culture container was constructed by attaching a mesh sheet prepared with polyester to the bottom of a plastic container having a total volume of 200 ml. 150 ml of *Tetraselmis* (wet weight of about 0.25 g/l) was placed in the culture container, and the culture container was allowed to be floated on an acryl water bath containing 40 l of natural seawater. Experimental groups were divided into 3 groups, and 1, 2, or 3 l/day of natural seawater were respectively introduced through a solution quantity regulator, while the control was allowed to be floated without additional supply of natural seawater such that nutrients were provided only through diffusion. To maintain nutrients in natural seawater consistent, 40 l of natural seawater was replaced once a day. During the culture, 200 µE/m²/s of light was supplied by using a fluorescent light for 24 hours, and culturing temperature was maintained at 20° C. Growth of microalgae was checked by measuring the volume of culture solution and cell wet weight in the culture solution daily. Also, pH in the culture solution was measured to investigate whether the chemical composition in the culture solution was well maintained or not depending on supply of environmental water. Consequently, as shown in FIG. 28, microalgae production was increased as supply of natural seawater (environmental water) increased. When 3 l/day of environmental water was supplied for 7 days of culture, an average microalgae productivity was increased by 199% (from 0.080 g/l/day for the control where environmental water was not supplied to 0.24 g/l/day) (FIGS. 28 and 29). On day 2 of the culture, microalgae cell wet weights in the reactors were low, thereby causing nutrition saturation, so that microalgae productivities of all experimental groups were 0.2 g/l showing no difference between each other. However, on 2-4 days of the culture, since environmental water supply was increased from 0 to 3 l/day, microalgae wet weights were respectively increased to 0.1, 0.2, 0.3 or 0.4 g/l which demonstrates that microalgae productivity was increased depending on environmental water supply (FIG. 28). In addition, through the pH value, it has been found that the chemical composition of the culture solution similar to that of fresh culture solution is maintained as environmental water supply increases (FIG. 30).

The minimal environmental water supply required to enhance culturing efficiency, which may be expressed by the following equation, varies depending on nutrient concentration in the environmental water and the boundary surface restricting free pass of cells, but allowing of pass of nutrients (e.g., a mesh sheet or perforated sheet).

$$V_{min} = \frac{K_p \cdot A}{C_{salt}}$$

Wherein, $V_{min}$ indicates minimal environmental water supply (k/day); $K_p$ indicates maximum penetration of nutrients (carbon, nitrogen, or phosphorous) at boundary surface in the environmental water (mg/m²/day); A indicates a surface area immersed in environmental water (m²); and $C_{salt}$ indicates nutrient concentration (mg/l) of environmental water outside of the reactor.

Example 9: Experiment of Culturing Microalgae *Tetraselmis* Sp. KCTC12236BP Through Supply of Natural Seawater at Enlarged Scale To demonstrate that microalgae productivity may be increased through environmental water supply at an enlarged scale, a culturing experiment was performed by using a raceway pond at outside. A culture container was constructed by cutting a plastic container having a total volume of 6 and covering five faces except the upper face with a mesh sheet prepared with polyester. 3 l of *Tetraselmis* (dry weight of about 0.006 g/l) was placed in the culture container, and the culture container was allowed to be floated on a raceway containing 1 tone of natural seawater. For "seawater supply" group, 10, 40, or 160 l/day of natural seawater contained in raceway was supplied depending on period of culture and concentration of microalgae. Natural seawater in the raceway was periodically replaced such that microorganisms other than microalgae were accumulated. As controls, "diffusion" group which uses the same culture container without natural seawater supply, and "nonpermeable" group which uses a plastic container as a culture container in which nutritional salts were not exchanged were used. Growth of microalgae was checked by measuring the volume of culture solution and cell wet weight in the culture solution daily. Also, salinity in the culture solution was measured to investigate whether the chemical composition in the culture solution was well maintained or not. Consequently, as shown in FIG. 31, it has been found that microalgae productivity was the highest when natural seawater was supplied, and microalgae concentration in the "nonpermeable" group in which nutritional salts penetration does not occur was decreased after slight increase. Based on 13-17 days of culture, maximal microalgae productivity per unit area per day of the experiment in which natural seawater was supplied was increased to 10 g/m²/day which was about 6 times of that of experimental group (i.e., 1.7 g/m²/day) in which natural seawater was not supplied during the same period of time (FIG. 31). In addition, it has been found that, under the rainfall condition, salinities of the culture solutions of "nonpermeable" group and "diffusion" group were reduced while salinity of the culture solution was not reduced when natural seawater was continuously supplied and maintained at a similar level to that of the raceway (FIG. 32).

APPENDIX 101-109, 209, 1100: Photobioreactor
110: Culture container
110': Open-type culture container
111, 211: Mesh sheet or perforated sheet
112: Axis
113, 213: Upper frame
114, 214: Vertical frame
115, 215: Lower frame
116, 216: Bottom wall
117, 217: Side wall
120, 220: Floating unit
130: Coupling unit
140: Sedimentation unit
150: Switching unit
160: Light blocking area
170, 170', 170": Fan
210: Raceway pond-type culture container
218: Partition
219: Culture solution circulator
1000: Microalgae culturing field
1200: Floating structure
1210: Culturing field upper frame
1211: Culturing field vertical frame
1212: Culturing field lower frame
1213: Culturing field floating unit
1220: Fence
1221: Bottom face

The invention claimed is:

1. A method for culturing microalgae, comprising:
(a) immersing a photobioreactor including a culture container through which a culture solution, but not microalgae, passes into environmental water; and
(b) supplying additional environmental water into the culture container, wherein the culture container comprises a boundary surface including a mesh sheet or a perforated sheet, and wherein the environmental water is supplied at 0.38 to 50000 l/day per m² of the mesh sheet or the perforated sheet.

2. The method for culturing microalgae of claim 1, wherein, in step (b), the environmental water is supplied in an amount calculated from the following equation:

$$V_{min} = \frac{K_p \cdot A}{C_{salt}}$$

wherein, $V_{min}$ indicates minimal environmental water supply (l/day); $K_p$ indicates maximum penetration of nutrients at boundary surface in the environmental water (mg/m²/day); A indicates a surface area of the mesh sheet or the perforated sheet immersed in environmental water (m²); and $C_{salt}$ indicates nutrient concentration of environmental water at the outside of culture container (mg/l).

3. The method for culturing microalgae of claim 1, wherein the environmental water is supplied at 670 to 2000 l/day per m² of the mesh sheet or the perforated sheet.

4. The method for culturing microalgae of claim 1, wherein the environmental water is sea water, plain water, brackish water, domestic sewage, artificially prepared medium, or eutrophic contaminated water.

5. The method for culturing microalgae of claim 4, wherein the sea water is artificial sea water or natural sea water.

6. The method for culturing microalgae of claim 1, wherein the microalgae are dispersed and cultured in a culture medium without a carrier.

7. The method for culturing microalgae of claim 1, wherein a whole or part of the boundary surface of the culture container has a mesh sheet having a mesh size of 0.1 to 200 μm or a perforated sheet having micropores of size of 0.1 to 200 μm.

8. The method for culturing microalgae of claim 6, wherein, except the boundary surface having the mesh sheet or the perforated sheet, the remainder boundary surface of the culture container has a nonpermeable or semipermeable and transparent or translucent material.

9. The method for culturing microalgae of claim 1, wherein the photobioreactor is floated on the water surface by a flotation unit or sedimented in the water by a sedimentation unit.

10. The method for culturing microalgae of claim 1, wherein the culture container comprises a light blocking cover on the upper part which regulates light energy supplied to microalgae.

11. The method for culturing microalgae of claim 1, wherein a plurality of the photobioreactors are coupled to each other.

12. The method for culturing microalgae of claim 1, wherein the microalgae strain is one or more selected from the group consisting of *Chlorella, Chlamydomonas, Haematococous, Botryococcus, Scenedesmus, Spirulina, Tetraselmis, Dunaliella, Nannochloropsis, Synechococcus, Synechocystis, Nostoc, Phaeodactylum, Porphyridium, Neochloris, Chaetoceros, Isochysis, Thalassiosira, stichococcus, pyramimonas, oscillatoria, Oocystis, ochromonas, navicula, chlorococcum* and *Nitzschia*.

13. The method for culturing microalgae of claim 1, wherein the supplying additional environmental water in step (b) is performed by using a wave pump, a sling pump, a wheel pump, a water hammer pump, a wind pump, or a solar photovoltaic pump.

* * * * *